United States Patent
Huang et al.

(10) Patent No.: US 8,426,120 B2
(45) Date of Patent: Apr. 23, 2013

(54) HIGH-THROUGHPUT IMAGING OF GRAPHENE BASED SHEETS BY FLUORESCENCE QUENCHING MICROSCOPY AND APPLICATIONS OF SAME

(75) Inventors: Jiaxing Huang, Wilmette, IL (US); Jaemyung Kim, Evanston, IL (US); Laura J. Cote, Chicago, IL (US); Franklin J. Kim, Wadsworth, IL (US)

(73) Assignee: Northwestern University, Evanston, IL (US)

( * ) Notice: Subject to any disclaimer, the term of this patent is extended or adjusted under 35 U.S.C. 154(b) by 358 days.

(21) Appl. No.: 12/893,470

(22) Filed: Sep. 29, 2010

(65) Prior Publication Data

US 2011/0076467 A1    Mar. 31, 2011

Related U.S. Application Data

(60) Provisional application No. 61/246,596, filed on Sep. 29, 2009.

(51) Int. Cl.
G03F 7/20    (2006.01)

(52) U.S. Cl.
USPC .......................................... 430/322

(58) Field of Classification Search .......... 430/311, 430/322
See application file for complete search history.

(56) References Cited

PUBLICATIONS

Novoselov, K.S. et al., Electric Field Effect in Atomically Thin Carbon Films, Science, 2004, vol. 306, 666-669.
Allen, M.J. et al., Honeycomb Carbon: A Review of Graphene, Chem. Rev., 2010, vol. 110, 132-145.
Park, S. et al., Chemical Methods for the Production of Graphenes, Nature Nanotech, 2009, vol. 4, 217-225.
Geim, A.K., Graphene: Status and Prospects, Science, 2009, vol. 324, 1530-1534.
Kim, K.S. et al., Large-Scale Pattern Growth of Graphene Films for Stretchable Transparent Electrodes, Nature, 2009, vol. 457, 706-710.
Li, X.L. et al., Chemically Derived, Ultrasmooth Graphene Nanoribbon Semiconductors, Science, 2008, vol. 319, 1229-1232.
Gilje, S. et al., A Chemical Route to Graphene for Device Applications, Nano Letters, 2007, vol. 7, No. 11, 3394-3398.
Li, X.L. et al., Highly Conducting Graphene Sheets and Langmuir-Blodgett Films, Nature Nanotech, 2008, vol. 3, 538-542.
Wang, X. et al., Transparent, Conductive Graphene Electrodes for Dye-Sensitized Solar Cells, Nano Letters, 2008, vol. 8, No. 1, 323-327.
Watcharotone, S. et al., Graphene-Silica Composite Thin Films as Transparent Conductors, Nano Letters, 2007, vol. 7, No. 7, 1888-1892.

(Continued)

*Primary Examiner* — Brittany Raymond
(74) *Attorney, Agent, or Firm* — Morris, Manning & Martin, LLP; Tim Tingkang Xia, Esq.

(57) ABSTRACT

A method for imaging a graphene-based film. In one embodiment, the method includes the steps of providing a graphene-based film on a surface of a medium; forming a fluorescent coating over the graphene-based film to form a sample; illuminating the sample with light of a specific wavelength or wavelengths, which is absorbed by the fluorescent coating to cause the fluorescent coating to emit light of wavelengths longer than that of the absorbed light, which is quenched by the graphene-based film such that a visibility contrast is formed between the graphene-based film and the fluorescent coating; and imaging the graphene-based film from the visibility contrast.

26 Claims, 14 Drawing Sheets

PUBLICATIONS

Eda, G. et al., Large-Area Ultrathin Films of Reduced Graphene Oxide as a Transparent and Flexible Electronic Material, Nature Nanotech, 2008, vol. 3, 270-274.

Tung, V.C. et al., High-Throughput Solution Processing of Large-Scale Graphene, Nature Nanotech, 2009, vol. 4, 25-29.

Stankovich, S. et al., Graphene-Based Composite Materials, Nature, 2006, vol. 442, 282-286.

Ramanathan, T. et al., Functionalized Graphene Sheets for Polymer Nanocomposites, Nature Nanotech, 2008, vol. 3, 327-331.

Dobelle, W.H. et al., Chemically Cleaved Graphite Support Films for Electron Microscopy, J. Cell Biol., 1968, vol. 39, 733-735.

Meyer, J.C. et al., Imaging and Dynamics of Light Atoms and Molecules on Graphene, Nature, 2008, vol. 454, 319-322.

Lee, Z. et al., Direct Imaging of Soft-Hard Interfaces Enabled by Graphene, Nano Letters, 2009, vol. 9, No. 9, 3365-3369.

Emtsev, K.V. et al., Towards Wafer-Size Graphene Layers by Atmospheric Pressure Graphitization of Silicon Carbide, Nature Materials, 2009, vol. 8, 203-207.

Yu, Q.K. et al., Graphene Segregated on Ni Surfaces and Transferred to Insulators, Applied Physics Letters, 2008, vol. 93, 113103-113103-3.

Li, X.S. et al., Large-Area Synthesis of High-Quality and Uniform Graphene Films on Copper Foils, Science, 2009, vol. 324, 1312-1314.

Reina, A. et al., Large Area, Few-Layer Graphene Films on Arbitrary Substrates by Chemical Vapor Deposition, Nano Letters, 2009, vol. 9, No. 1, 30-35.

Hirata, M. et al., Thin-Film Particles of Graphite Oxide 1: High-Yield Synthesis and Flexibility of the Particles, Carbon, 2004, vol. 42, 2929-2937.

Dikin, D.A. et al., Preparation and Characterization of Graphene Oxide Paper, Nature, 2007, vol. 448, 457-460.

Stankovich, S. et al., Synthesis of Graphene-Based Nanosheets Via Chemical Reduction of Exfoliated Graphite Oxide, Carbon, 2007, vol. 45, 1558-1565.

Hummers, W.S. et al., Preparation of Graphite Oxide, J. Am. Chem. Soc., 1958, vol. 80, 1339.

Gao, W. et al., New Insights into the Structure and Reduction of Graphite Oxide, Nature Chemistry, 2009, vol. 1, 403-408.

Widenkvist, E. et al., Mild Sonochemical Exfoliation of Bromine-Intercalated Graphite: A New Route Towards Graphene, J. Phys. D: Appl. Phys., 2009, vol. 42, 1-5.

Hernandez, Y. et al., High-Yield Production of Graphene by Liquid-Phase Exfoliation of Graphite, Nature Nanotech, 2008, vol. 3, 563-568.

Choucair, M. et al., Gram-Scale Production of Graphene Based on Solvothermal Synthesis and Sonication, Nature Nanotech, 2009, vol. 4, 30-33.

Kim J. et al., Visualizing Graphene Based Sheets by Fluorescence Quenching Microscopy, J. Am. Chem. Soc., 2010, vol. 132, 260-267.

Nair R.R. et al., Fine Structure Constant Defines Visual Transparency of Graphene, Science, 2008, vol. 320, 1308.

Jung, I. et al., Simple Approach for High-Contrast Optical Imaging and Characterization of Graphene-Based Sheets, Nano Letters, 2007, vol. 7, No. 12, 3569-3575.

Roddaro, S. et al., The Optical Visibility of Graphene: Interference Colors of Ultrathin Graphite on SiOs, Nano Letters, 2007, vol. 7, No. 9, 2707-2710.

Jung, I. et al., Characterization of Thermally Reduced Graphene Oxide by Imaging Ellipsometry, J. Phys. Chem., 2008, vol. 112, 8499-8506.

Stolyarova, E. et al., High-Resolution Scanning Tunneling Microscopy Imaging of Mesoscopic Graphene Sheets on an Insulating Surface, Proc. Natl. Acad. Sci., 2007, vol. 104, 9209-9212.

Cote, L.J. et al., Langmuir-Blodgett Assembly of Graphite Oxide Single Layers, J. Am. Chem. Soc., 2009, vol. 131, 1043-1049.

Ferrari, A.C. et al., Raman Spectrum of Graphene and Graphene Layers, Physical Review Letters, 2006, vol. 97, 187401-1-187401-4.

Graf, D. et al., Raman Imaging of Graphene, Solid State Communications, 2007, vol. 143, 44-46.

Calizo, I. et al., Raman Nanometrology of Graphene: Temperature and Substrate Effects, Solid State Communications, 2009, vol. 149, 1132-1135.

Krauss, B. et al., Laser-Induced Disassembly of a Graphene Single Crystal into a Nanocrystalline Network, Physical Review, 2009, vol. 79, 165428-1-165428-9.

Cote, L.J. et al., Flash Reduction and Patterning of Graphite Oxide and Its Polymer Composite, J. Am. Chem. Soc., 2009, vol. 131, 11027-11032.

Jung, I. et al., Tunable Electrical Conductivity of Individual Graphene Oxide Sheets Reduced at "Low" Temperatures, Nano Letters, 2008, vol. 8, No. 12, 4283-4287.

Hwa, T. et al., Conformation of Graphite Oxide Membranes in Solution, Physical Review A, 1991, vol. 44, No. 4, 44, R2235-R2240.

Wen X. et al., Crumpled and Collapsed Conformations in Graphite Oxide Membranes, Nature, 1992, vol. 355, 426-428.

Spector, M.S. et al., Conformations of a Tethered Membrane: Crumpling in Graphite Oxide, Physical Review Letters, 1994, vol. 73, No. 21, 2867-2872.

Sun, X. et al., Nano-Graphene Oxide for Cellular Imaging and Drug Delivery, Nano Res., 2008, vol. 1, 203-212.

Llopis, J. et al., Measurement of Cytosolic, Mitochondrial, and Golgi pH in Single Living Cells with Green Fluorescent Proteins, Proc. Natl. Acad. Sci., 1998, vol. 95, 6803-6808.

Liangwei, Q. et al., Interactions of Functionalized Carbon Nanotubes with Tethered Pyrenes in Solution, J. Chem. Phys., 2002, vol. 117, 8089-8094.

Nakayama-Ratchford, N. et al., Noncovalent Functionalization of Carbon Nanotubes by Fluorescein-Polyethylene Glycol: Supramolecular Conjugates with pH-Dependent Absorbance and Fluorescence, J. Am. Chem. Soc., 2007, vol. 129, 2448-2449.

Kagan, M.R. et al., Reduction of Fluorescence Interference in Raman Spectroscopy via Analyte Adsorption on Grpahitic Carbon, Analytical Chemistry, 1994, vol. 66, 4159-4165.

Swathi R.S. et al., Resonance Energy Transfer from a Dye Molecule to Graphene, J. Chem. Phys., 2008, vol. 129, 054703-1-054703-9.

Swathi, R.S. et al., Long Range Resonance Energy Transfer from a Dye Molecule to Graphene has (distance)-4 Dependence, J. Chem. Phys., 2009, vol. 130, 086101-1-086101-3.

Xu, Y.F. et al., A Graphene Hybrid Material Covalently Functionalized with Porphyrin: Synthesis and Optical Limiting Property, Advanced Materials, 2009, vol. 21, 1275-1279.

Didenko, V.V. et al., Visualization of Individual Single-Walled Carbon Nanotubes by Fluorescent Polymer Wrapping, Nano Letters, vol. 5, No. 8, 1563-1567.

Turro N.J. et al., Principles of Molecular Photochemistry: An Introduction, University Science Books: Sausalito, Calif., 2009, 495.

Treossi, E. et al., High-Contrast Visualization of Graphene Oxide on Dye-Sensitized Glass, Quartz, and Silicon by Fluorescence Quenching, J. Am. Chem. Soc., 2009, vol. 131, 15576-15577.

Israelachvili, J.N, Intermolecular and Surface Forces, 2nd ed., Academic Press. 1992, 450.

Luo, Z.T. et al., High Yield Preparation of Macroscopic Graphene Oxide Membranes, J. Am. Chem. Soc., 2009, vol. 131, 898-899.

Li, D. et al., Processable Aqueous Dispersions of Graphene Nanosheets, Nature Nanotech, 2008, vol. 3, 101-105.

Becerril, H.A. et al., Evaluation of Solution-Processed Reduced Graphene Oxide Films as Transparent Conductors, ACS Nano, 2008, vol. 2, No. 3, 463-470.

Danauskas, S.M. et al., Monitoring X-Ray Beam Damage on Lipid Films by an Integrated Brewster Angle Microcope/X-Ray Diffractometer, Review of Scientific Instruments, 2007, vol. 78, 103705-1-103705-9.

Marshall, G. et al., A Compact Brewster-Angle Microscope for Use in Langmuir-Blodgett Deposition, Review of Scientific Instruments, 1998, vol. 69, 3699-3700.

Kim, F. et al., Graphene Oxide: Surface Activity and Two-Dimensional Assembly, Advanced Materials, 2010, vol. 22, 1954-1958.

Love, J.C. et al., Microscope Projection Photolithography for Rapid Prototyping of Masters with Micron-Scale Features for Use in Soft Lithography, Languir, 2001, vol. 17, 6005-6012.

Table 1 Current imaging techniques for visualizing graphene-based sheets.

| Techniques | Mechanism | Relative speed | Requirement on substrate | Solution observation | Other requirement |
|---|---|---|---|---|---|
| Optical Microscopy | Interference | Fast | Dielectrics coated Si | No | Optimized dielectric thickness and wavelength |
|  | Ellipsometry | Fast | Dielectrics coated Si | No |  |
| AFM | Force between sample and tip | Low (scanning) | Smooth surface (e.g., Si, mica, quartz) | No | Vibration isolation |
| STM | Electron tunneling | Low (scanning) | Conductive, atomically smooth | No | Vacuum |
| SEM | Secondary and scattered electrons | Medium (scanning) | Conductive | No | Vacuum |
| TEM | Absorbed electrons | Slow | Transparent to electron | No | Vacuum |
| Raman | Inelastic photon scattering | Fast | Low fluorescence, effective heat dissipation | No | Laser |

FIG. 11

HIGH-THROUGHPUT IMAGING OF GRAPHENE BASED SHEETS BY FLUORESCENCE QUENCHING MICROSCOPY AND APPLICATIONS OF SAME

CROSS-REFERENCE TO RELATED APPLICATIONS

This application claims the benefit, pursuant to 35 U.S.C. §119(e), of U.S. provisional patent application Ser. No. 61/246,596 filed Sep. 29, 2009, entitled "HIGH-THROUGHPUT IMAGING OF GRAPHENE BASED SHEETS BY FLUORESCENCE QUENCHING MICROSCOPY," by Jiaxing Huang, Jaemyung Kim, Laura J. Cote and Franklin J. Kim, which is incorporated herein by reference in its entirety.

STATEMENT REGARDING FEDERALLY SPONSORED RESEARCH OR DEVELOPMENT

This invention was made with government support under Grant No. EEC 0647560 awarded by the National Science Foundation (NSEC). The government has certain rights in the invention.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, superscript "n" represents the nth reference cited in the reference list. For example, ( )[30] represents the 30th reference cited in the reference list, namely, [30], Kim, J., et al., *J. Am. Chem. Soc.* (2010), 132 (1), 260.

FIELD OF THE INVENTION

The present invention relates generally to imaging a graphene-based film, in particular, to methods of imaging a graphene-based film through inventive fluorescence quenching microscopy, and applications of same.

BACKGROUND OF THE INVENTION

Graphene is two-dimensional nanomaterial consisting of a single layer of $sp^2$ network of carbon atoms as shown in FIG. 1(*a*)[1]. Microscopy imaging is indispensable for characterizing these single atomic layers, and oftentimes is the first measure of sample quality. While the thickness of a graphene sheet is on the order of a single atomic unit, its lateral dimension can approach up to tens of microns. Graphene and its derivatives such as graphene oxide (GO) as shown in FIG. 1(*b*), and reduced graphene oxide (r-GO, a.k.a. chemically modified graphene) as shown in FIG. 1(*c*) have attracted great interests in both fundamental science and technology due to their intriguing structures and excellent electronic, mechanical and thermal properties[2-4]. Graphene-based sheets (GBS) have been shown to be very promising for high-performance nanoelectronics[1,5-7], transparent conductor[8-12], polymer composite[13,14] and electron microscopy support[15-17], etc. Initially graphene was discovered and prepared at the individual sheet level by mechanical exfoliation from highly ordered pyrolytic graphite (HOPG) crystals—the so-called Scotch tape trick[1]. To scale up the production, various synthetic methods are being developed. At a slightly larger "single substrate" scale, high quality graphene thin films have been prepared epitaxially on SiC surface[18], and most recently by chemical vapor deposition (CVD) on catalytic metal surfaces[5,19-21]. At an even larger scale, bulk production typically yields GBS in forms of solvent dispersion, which can then be used by solution processing techniques in various forms. Some recent success includes chemical exfoliation through the formation of derivatized graphene sheets such as GO[22-25], r-GO[12,26] or halogenated graphene[27], solvent assisted ultrasonic exfoliation28 and solvothermal reduction of organic solvent using alkali metals[29].

GBS are essentially the world's thinnest materials: they are single atomic layers with lateral dimension extends from nanometers well into tens of microns. The first characterization step typically involves microscopy imaging to determine the presence of single layers, and their sizes and position on the substrate. It is an indispensable quality control tool for manufacturing GBS materials since it can provide immediate feedback to improve synthetic and processing strategies.

This is especially important for single sheet level research, which starts from selecting proper GBS pieces for further experiments. Imaging is also crucial for evaluating the microstructures of solution processed GBS thin films such as surface coverage, degree of wrinkles, overlaps, and folds of individual sheets, which heavily affect the overall material properties. Therefore, developing a high-throughput, low-cost, general imaging technique that allows quick evaluation of GBS materials would be highly desirable as it could boost the R&D capability from a fundamental level.

Therefore, a heretofore unaddressed need exists in the art to address the aforementioned deficiencies and inadequacies.

BRIEF SUMMARY OF THE INVENTION

In one aspect, the present invention provides a method for imaging a graphene-based film. In one embodiment, the method includes the steps of (a) providing a graphene-based film on a surface of a medium;

(b) forming a fluorescent coating over the graphene-based film to form a sample;

(c) illuminating the sample with light of a specific wavelength or wavelengths, which is absorbed by the fluorescent coating to cause the fluorescent coating to emit light of wavelengths longer than that of the absorbed light, which is quenched by the graphene-based film such that a visibility contrast is formed between the graphene-based film and the fluorescent coating; and (d) imaging the graphene-based film from the visibility contrast.

In one embodiment, the graphene-based film comprises at least one of a GO sheet, a r-GO sheet, and a graphene sheet.

In one embodiment, the fluorescent coating comprises one of a dye layer and a dye and polymer layer. The dye comprises fluorescein, 4-(dicyanomethylene)-2-methyl-6-(4-dimethylaminostyryl)-4H-pyran, and 2,5-bis(5-tert-butyl-2-benzoxazolyl)thiophene. And the polymer comprises one of polyvinylpyrrolidone (PPV), poly(methyl methacrylate) (PMMA), and SU-8.

The medium can be solid or liquid. In one embodiment, the solid medium comprises a substrate. The substrate can be a conductive substrate, a semi-conductive substrate such as a silicon wafer, or insulative substrate such as a glass.

In one embodiment, the liquid medium comprises a solution such as water.

The visibility contrast, C, formed between the graphene-based film and the fluorescent coating satisfies the following relationship:

$$C=(I_B-I_G)/I_B,$$

wherein $I_B$ and $I_G$ are the optical intensities of the fluorescent coating and the graphene-based film in the imaging, and wherein $I_B > I_G$.

In one embodiment, the light of a specific wavelength or wavelengths is delivered from a light source of a fluorescence microscope. The light of a specific wavelength or wavelengths is delivered onto the fluorescent coating during the illuminating step. The fluorescent coating has a thickness d<200 nm.

In one embodiment, the method further includes the step of determining a thickness or a number of layers of the graphene-based film from the imaging of the graphene-based film.

In another aspect, the present invention provides a method for forming a pattern on a graphene-based film. In one embodiment, the method includes the steps of (a) providing a graphene-based film supported by a substrate, wherein the graphene-based film has one or more GO sheets or r-GO sheets or graphene sheets;

(b) forming a fluorescent photoresist coating over the graphene-based film to form a sample;

(c) illuminating the sample with light of a first wavelength or wavelengths along an optical path such that a visibility contrast is formed between the graphene-based film and the fluorescent photoresist coating;

(d) imaging the graphene-based film from the visibility contrast to select a desired GO sheet or r-GO sheet or graphene sheet;

(e) inserting a photo mask in front of the selected GO sheet or r-GO sheet or graphene sheet along the light path, wherein the photo mask is formed with a plurality of windows that are transparent to optical energy, and wherein the plurality of windows is arranged according to a desired pattern; and (f) illuminating the photo mask with light of a second wavelength or wavelengths along the optical path to irradiate the sample by the optical energy passing through the plurality of windows of the photo mask to expose the fluorescent photoresist coating and form a pattern corresponding to the desired pattern on the selected GO sheet or r-GO sheet or graphene sheet.

In one embodiment, the substrate is formed from glass.

In one embodiment, the fluorescent photoresist coating comprises a dye and polymer layer. The dye and polymer layer can be one of dye doped photoresist SU-8 layer and photoresist poly(methyl methacrylate) (PMMA) layer. As formed, the fluorescent photoresist coating layer contains a plurality of fluorescent dye molecules.

The visibility contrast, C, formed between the graphene-based film and the fluorescent photoresist coating satisfies the following relationship:

$$C=(I_B-I_G)/I_B,$$

where $I_B$ and $I_G$ are the optical intensities of the fluorescent photoresist coating and the graphene-based film in the imaging, and wherein $I_B > I_G$.

The first specific wavelength is greater than 520 nm. In one embodiment, the light of the first specific wavelength is a green light with a frequency in a range of from about 520 nm to about 565 nm.

The second specific wavelength is smaller than the first specific wavelength. The second specific wavelength is smaller than 500 nm. In one embodiment, the light of the second specific wavelength is an ultraviolet light with a frequency in a range of from about 10 nm to about 400 nm.

In one embodiment, the light of the first specific wavelength is delivered from a light source with a first filter cube, and the light of the second specific wavelength is delivered from the light source with a second filter cube.

The graphene-based film with a pattern as formed has a conducting area and an insulating area, and wherein the conducting area is formed with a pattern corresponding to the plurality of windows arranged according to a desired pattern by being exposed to the optical energy delivered through the plurality of windows of the mask, and the insulating area is formed corresponding to the areas of the mask where the plurality of windows are not located at, respectively. In one embodiment, the conducting area comprises an array of electrodes.

In another aspect, the present invention provides an article of manufacture made by the method as set forth immediately above.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

FIG. 11 displays Table 1 for current imaging techniques for visualizing graphene-based sheets.

DETAILED DESCRIPTION OF THE INVENTION

Figure 1:
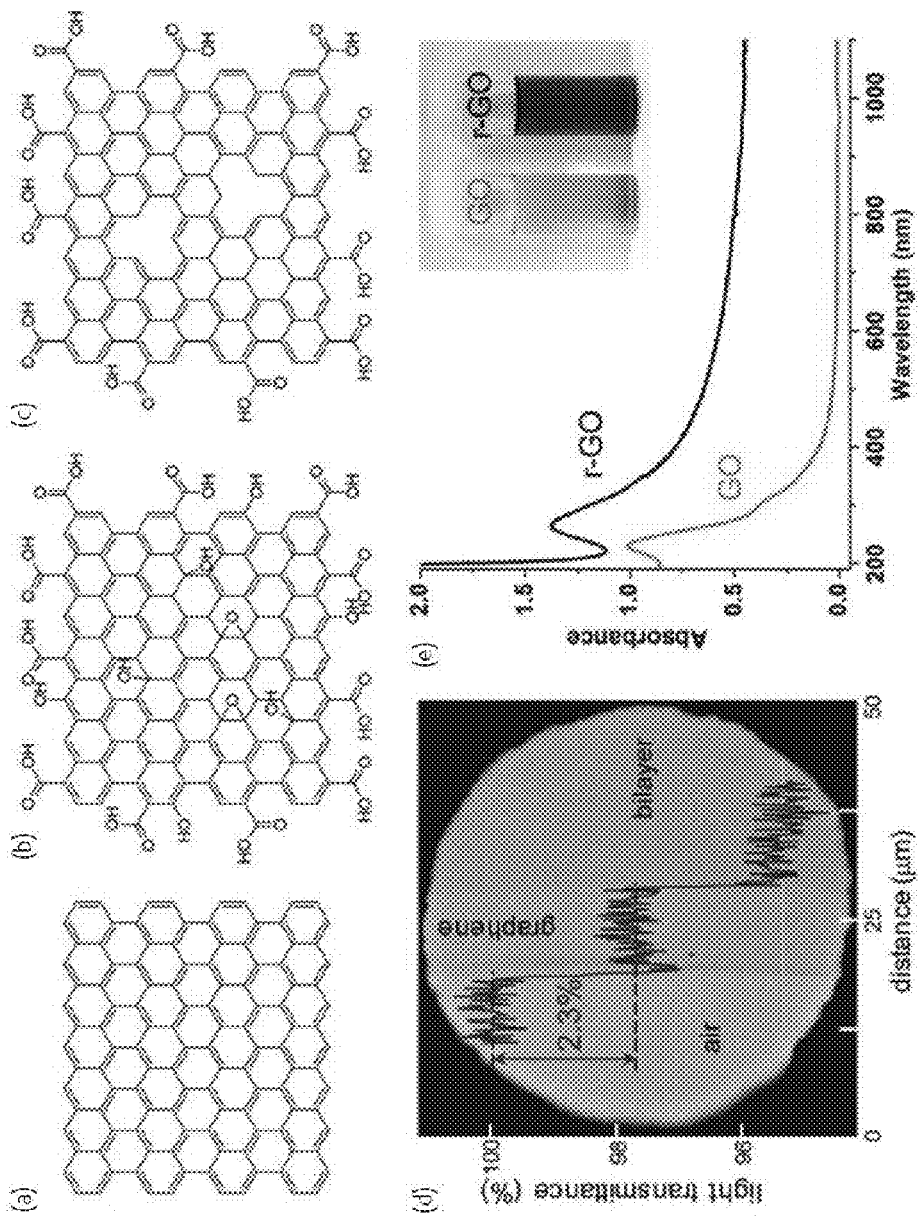
FIG. 1 schematically shows (a) a structural model of graphene; (b) a structural model of graphene oxide (GO); (c) a structural model of reduced graphene oxide (r-GO); (d) Optical absorbance of graphene is measured to be at 2.3% per single layer. The sample was supported on a porous membrane (courtesy of Rahul R. Nair)[31]; and (e) The optical absorbance of GO is much weaker than graphene or r-GO due to less degree of π-conjugation. The inset shows the color of the corresponding GO and r-GO dispersions of the same concentration, respectively.
Figure 2:
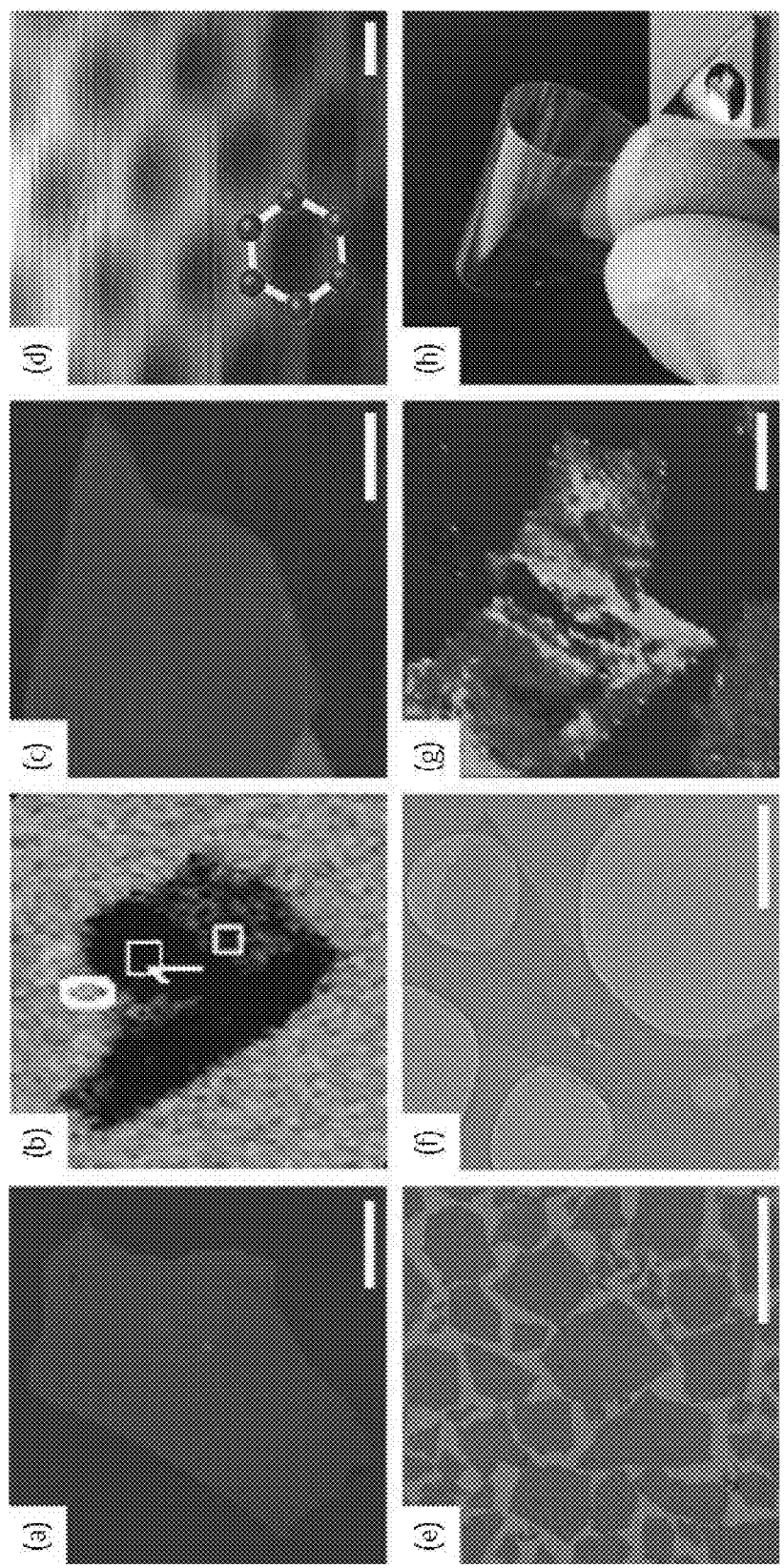
FIG. 2 schematically shows common microscopy techniques for imaging GBS. Optical microscopy images of graphene based on (a) interference (scale bar=20 μm) (adapted from 1, with permission, American Association for the Advancement of Science) and (b) ellipsometry (adapted from[34], with permission, ACS Publication), respectively. Both methods rely on dielectric coated silicon with proper thickness and optimal illuminating wavelength. (c) Atomic force microscopy (AFM, scale bar=1 μm) imaging of graphene sheet on SiO2 surface (adapted from 1, with permission, American Association for the Advancement of Science). AFM can give accurate height measurement on smooth surfaces but it is rather low-throughput. (d) Scanning tunneling microscopy (STM, scale bar=0.1 nm, adapted from 35, with permission, National Academy of Sciences, U.S.A.) can produce high-resolution, atomic-scale images. But it is too low-throughput for routine imaging. Electron microscopy, such as (e) scanning electron microscopy (SEM, scale bar=20 μm) and (f) transmission electron microscopy (TEM, scale bar=500 nm, adapted from 28, with permission, Nature Publishing Group) also needs to use special substrates for imaging GBS. (g) Raman imaging (scale bar=3 μm, adapted from[38], with permission, Elsevier) is particularly useful for identifying the number of layers for graphene samples. But substrates that have low intrinsic fluorescence and can efficiently dissipate laser heating are required. (h) No techniques are available yet for high-throughput imaging of GBS on plastic surfaces or even in solution (inset).
Figure 3:
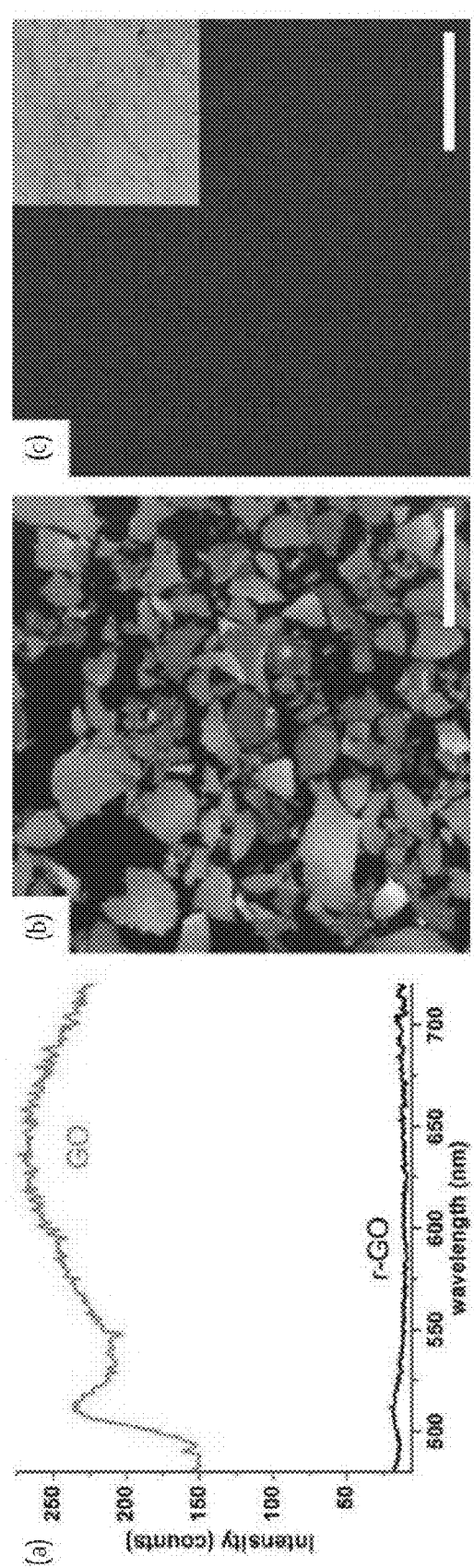
FIG. 3 show a direct fluorescence microscopy observation of GBS. (a) Fluorescence spectra of micron sized GO and r-GO sheets dispersed in water upon excitation at 400 nm. While GO has weak auto fluorescence in visible range (brown line), the corresponding r-GO is essentially not fluorescent at all. (b) and (c) are fluorescence microscopy (Nikon TE2000-U) images of GO and r-GO deposited on glass substrates, respectively, taken by a cooled CCD camera with exposure time of 10 s. (c) Although it is possible to acquire a fluorescence image of GO sheets, extended exposure time is needed, which makes it impractical for routine use. (d) r-GO sheets cannot be visualized at all under the same condition. The inset is a bright field transmission image of the r-GO sample in same area, showing the presence of many black islands of thick multilayers. Scale bars=50 μm.

The present invention is more particularly described in the following examples that are intended as illustrative only since numerous modifications and variations therein will be apparent to those skilled in the art. Various embodiments of the invention are now described in detail. Referring to the drawings, FIGS. 1-10, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, if any, the term "transmission electron microscopy (TEM)" refers to a microscopy technique whereby a beam of electrons is transmitted through an ultra thin specimen, interacting with the specimen as it passes through it. An image is formed from the electrons transmitted through the specimen, magnified and focused by an objective lens and appears on an imaging screen, a fluorescent screen in most TEMs, plus a monitor, or on a layer of photographic film, or to be detected by a sensor such as a CCD camera.

As used herein, if any, the term "scanning electron microscope (SEM)" refers to a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

As used herein, if any, the term "X-ray diffraction (XRD)" refers to a method of determining the arrangement of atoms within a crystal or solid, in which a beam of X-rays strikes a crystal and diffracts into many specific directions. From the angles and intensities of these diffracted beams, a crystallographer can produce a three-dimensional picture of the density of electrons within the crystal. From this electron density, the mean positions of the atoms in the crystal can be determined, as well as their chemical bonds, their disorder and various other information. In an X-ray diffraction measurement, a crystal or solid sample is mounted on a goniometer and gradually rotated while being bombarded with X-rays, producing a diffraction pattern of regularly spaced spots known as reflections. The two-dimensional images taken at different rotations are converted into a three-dimensional model of the density of electrons within the crystal using the mathematical method of Fourier transforms, combined with chemical data known for the sample.

More specifically, various techniques that have been used to visualize the single atomic GBS are further described herein.

Optical Microscopy

Regardless of the chemical composition, all GBS share one common structural feature—they are all essentially a single atomic layer. This makes the absorbance-based optical microscope observation very difficult. The optical absorbance of pristine graphene (a.k.a., mechanically exfoliated graphene) has been found to be 2.3% per single layer in the visible range[31]. Although it is possible to acquire optical images of suspended graphene sheets under bright field transmitted light as shown in FIG. 1(d), routine observation is difficult, especially when graphene is deposited on a substrate that increases the background absorption. This hinders the identification of graphene sheets on a substrate. GO has much paler color and even weaker optical absorbance than graphene as shown in FIG. 1(e), which practically prohibits its direct optical observation by eye under bright field illumination. Nevertheless, under reflective illumination, high-contrast optical imaging of graphene and even GO sheets has been demonstrated by interference-based techniques (FIG. 2a)[32,33] and imaging ellipsometry (FIG. 2b)[34], but only on dielectric-coated silicon wafers, where the thickness of the dielectrics (e.g., $SiO_2$ or $Si_3N_4$) and the illuminating wavelength need to be optimized. In fact, it is on such substrates that graphene was discovered in 2004 using an optical microscope under reflective illumination.

Scanning Probe Microscopy

Scanning probe based techniques have been widely used to image GBS materials, since its high resolution allows accurate height measurement at nanometer scale, which can be used to count the number of layers in a GBS. Among various types of scanning probe microscopy techniques, atomic force microscopy (AFM) as shown in FIG. 2(c) is most commonly used to characterize GBS. For instance, the thickness of a single layer GO sheet was experimentally measured to be around 1 nm by AFM[24]. It has become an essential piece of instrument for research in the GBS area. Scanning tunneling microscopy (STM) as shown in FIG. 2(d) is often used for imaging GBS when atomic scale resolution is needed[35]. The major disadvantage of scanning probe techniques is their low-throughput, making it costly and time-consuming for large-area sample examination. In addition, they need to operate on low-vibration platform and the samples need to be deposited on low roughness surface such as Si wafer, freshly cleaved mica, or quartz.

Electron Microscopy

Electron microscopy, especially scanning electron microscopy (SEM) is routinely used to image nanomaterials. It has become a quite standard, easy-to-use instrument that is capable to image GBS down to single layers as shown in FIG. 2(e)[36]. When an electron beam impinges on a sample, electron-matter interactions can produce a variety of products such as backscattered electrons (BSE), secondary electrons (SE), auger electrons, X-ray, and cathodoluminescence, which can be selectively collected and combined to generate images. BSE signal comes from elastically scattered, high energy incident electrons, and is sensitive to atomic composition of the specimen since heavier elements scatter more efficiently. Some incident electrons also experience inelastic scattering to transfer energy onto the specimen atoms, during which lower energy SE is emitted from the excited atoms. SE signal can generate high resolution images but is sensitive to surface charging. Therefore, insulating samples such as GO are harder to image with SE. FIG. 2(e) shows a SEM (Hitachi FE-SEM S-4800) image of insulating GO sheets deposited on a Si wafer with native oxide layer. The image was acquired by an in-chamber, lower detector positioned near the sample surface, which collects signals from both SE and BSE. In addition, the signal to noise ratio of lower detector images is better since it is closer to the sample surface. Thus it was found that SEM images of GO sheets acquired by lower detector are less affected by surface charging, and can be very "crispy" such as the one shown in FIG. 2(e). As a result, the inventors have been able to use SEM for high throughput examination of GO sheets over centimeter scale areas. However, the main drawback of SEM is that it works best for samples deposited on conducting substrates. Direct imaging of GO deposited on glass or plastic substrates has been extremely difficult. In addition, the electron beam can easily damage the GO sheets, especially when high acceleration voltages or short working distances are used, resulting in burnt spots and unwanted carbonaceous contamination. Transmission electron microscopy (TEM) as shown in FIG. 2(f) can offer insight into the local structures of GBS down to atomic level[28], but is a rather low-throughput technique. Both SEM and TEM require vacuum environment during operation.

Raman Imaging

Raman imaging as shown in FIG. 2(g) has been particularly useful for identifying the number of layers in a mechanically exfoliated graphene sample[37-39]. However, the sample needs to be deposited on low fluorescence substrates. Many plastic substrates have intrinsic fluorescence that could interfere or even overwhelm the Raman signals from single layers of GBS materials. Another concern is sample damage by laser heating as a recent study revealed that graphene could undergo local decomposition when irradiated with focused laser spots even at moderate power levels[40]. Laser heating will be more destructive for GO since it is known to be sensitive to light and heat[41,42].

New Imaging Challenges for GBS Materials

Nearly all the current imaging techniques rely on the use of special types of substrates as summarized in Table 1 shown in FIG. 11. Alternative methods that can produce high-contrast images of GBS on arbitrary surface should be highly desirable as it can meet the need for high-throughput sample evaluation in diverse applications as illustrated in part in FIG. 2(h). For example, solution-processed GO and r-GO sheets have been extensively studied for potential applications in flexible, plastic electronics. Although deposition on plastic substrates have been performed, it has been extremely difficult, if not impossible, to obtain high-contrast images on the insulating plastic substrates using current techniques. The lack of insight into the microstructures prevents people including those skilled in the art from quantitatively establishing parameters such as how processing conditions (e.g., dip-coating, spin-coating or spraying) and surface properties of the plastics affect the thin film properties.

Another challenge is solution phase imaging that is hardly achievable by the current imaging techniques. Such real-time observation of GBS should reveal many exciting "live" and "wet" phenomena. For example, it may help to study solvent induced conformation change in 2D tethered polymers such as GO. It could provide direct evidence whether a crumpled phase of GO exists[43-45]. It may reveal how GBS materials assemble under various conditions (e.g., temperature, ionic strength), which will greatly advance our knowledge of these 2D colloids. It could help to understand how to better control the size of sheets by watching how their size evolve during chemical treatment (e.g., solution phase oxidation and reduction). In addition, it will enable the observation of dewetting process of a GBS dispersion, which will offer insights for improving thin film processing techniques.

A third challenge is observing GBS sheets embedded in a polymer matrix for designing better composites. This can help to answer questions such as how the sheets disperse in the matrix and how they respond under external stress.

OVERVIEW OF THE INVENTION

The present invention answers these challenges and provides, among other things, a fluorescence quenching microscopy (FQM) technique that allows high-throughput, high contrast imaging of garphene-based sheets on arbitrary substrate and even in solution. As set forth in this disclosure, and as invented and developed according to several embodiments of the present invention, FQM presents itself as a general, low-cost imaging method that allows high-contrast, high-throughput visualization of GBS. Being an optical microscopy, it is not suitable for observing structures beyond diffraction limit. However, it is especially useful for quick sample check, which so far is heavily relying on AFM and SEM. Moreover, it enables new imaging capabilities on plastics and in solution. The highly versatile nature of FQM should make it a general imaging tool for characterizing graphene based materials, which should help to advance our understanding on the processing-structure property relationships of these 2D nanomaterials. In addition, the remote fluorescence quenching effect behind FQM could also make it useful for investigating molecule-graphene interactions at various separations.

Figures 4A, 4B, 4C:
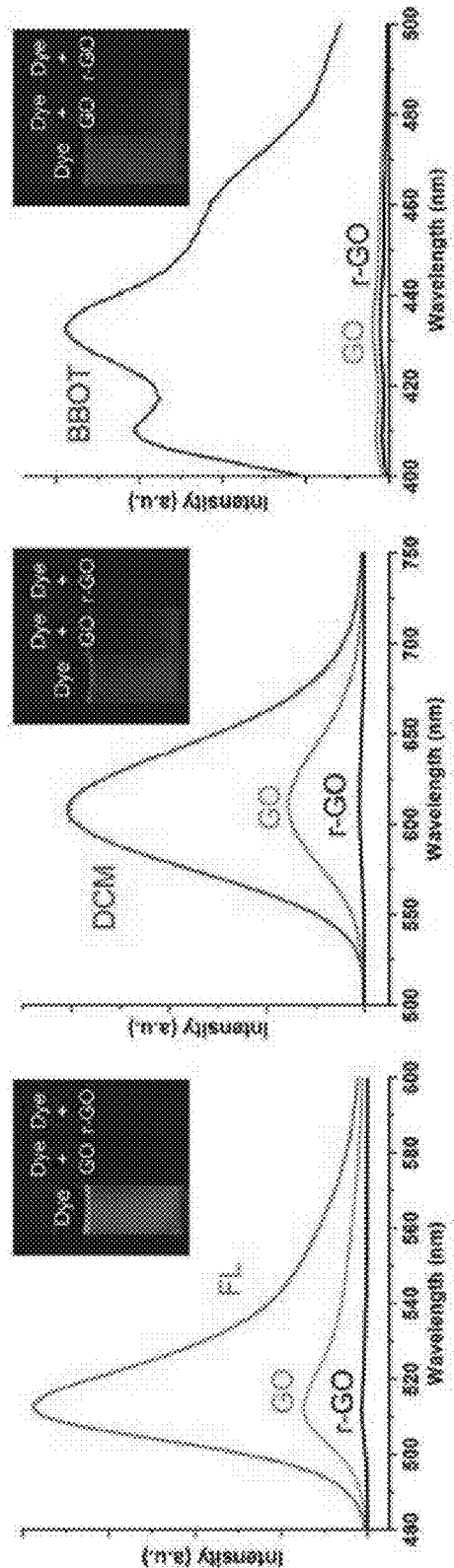
FIG. 4 shows an FQM for visualizing GBS according to one embodiment of the present invention. Upon the addition of small amount of GO and r-GO, the fluorescence of (A) fluorescein, (B) DCM and (C) BBOT becomes significantly reduced (insets). This result suggests that fluorescence quenching by GBS is a general phenomenon independent of the fluorescent dye used. (D) In a typical FQM experiment according to embodiments of the present invention, a fluorescent dye layer is applied onto a GBS covered substrate, which can reveal the underlying GBS upon excitation. (E) Schematic drawings of an inverted fluorescence microscopy system that has been used to demonstrate FQM. (F) FQM image of GO deposited on SiO2/Si substrate after exciting a fluorescein/PVP layer. It reveals vivid details of wrinkles, folds and overlaps of the GO sheets. Scale bar=50 μm.
Figure 4E:
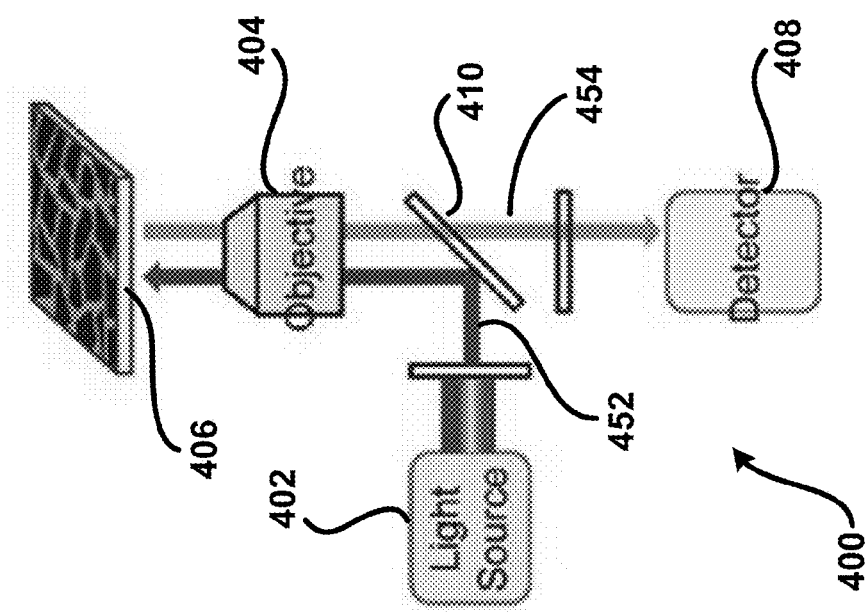
Figure 4D:
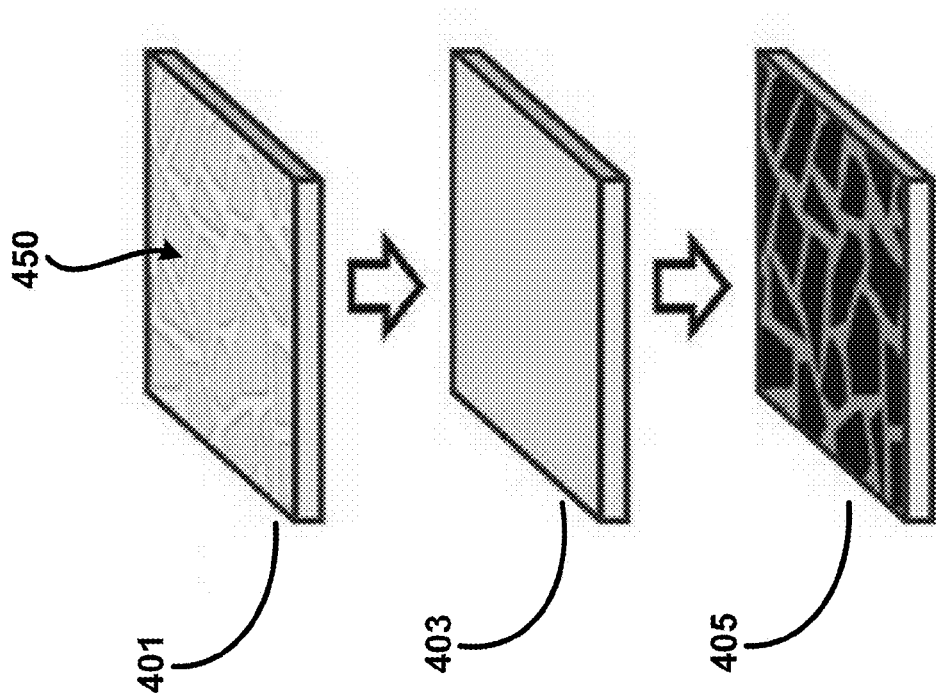

Thus, in one aspect, the present invention provides a method for method for imaging a graphene-based film. In one embodiment as shown in FIGS. 4(D) and 4(E), the method 450 includes the steps of (a) providing a graphene-based film on a surface of a medium at step 401;

(b) forming a fluorescent coating over the graphene-based film to form a sample 406 at step 403;

(c) at step 405, illuminating the sample 406 with light 452 of a specific wavelength or wavelengths, which is absorbed by the fluorescent coating to cause the fluorescent coating to emit light of wavelengths longer than that of the absorbed light, which is quenched by the graphene-based film such that a visibility contrast is formed between the graphene-based film and the fluorescent coating; and (d) imaging the graphene-based film from the visibility contrast.

In one embodiment, the graphene-based film comprises at least one of a GO sheet, a r-GO sheet, and a graphene sheet.

In one embodiment, the fluorescent coating comprises one of a dye layer and a dye and polymer layer. The dye comprises fluorescein, 4-(dicyanomethylene)-2-methyl-6-(4-dimethylaminostyryl)-4H-pyran, and 2,5-bis(5-tert-butyl-2-benzoxazolyl)thiophene.

And the polymer comprises one of polyvinylpyrrolidone (PPV), poly(methyl methacrylate) (PMMA), and SU-8.

The medium can be solid or liquid. In one embodiment as shown in FIGS. 4(D) and 4(E), the solid medium is a substrate. The substrate can be a conductive substrate, a semiconductive substrate such as a silicon wafer, or insulative substrate such as a glass.

Figure 9:
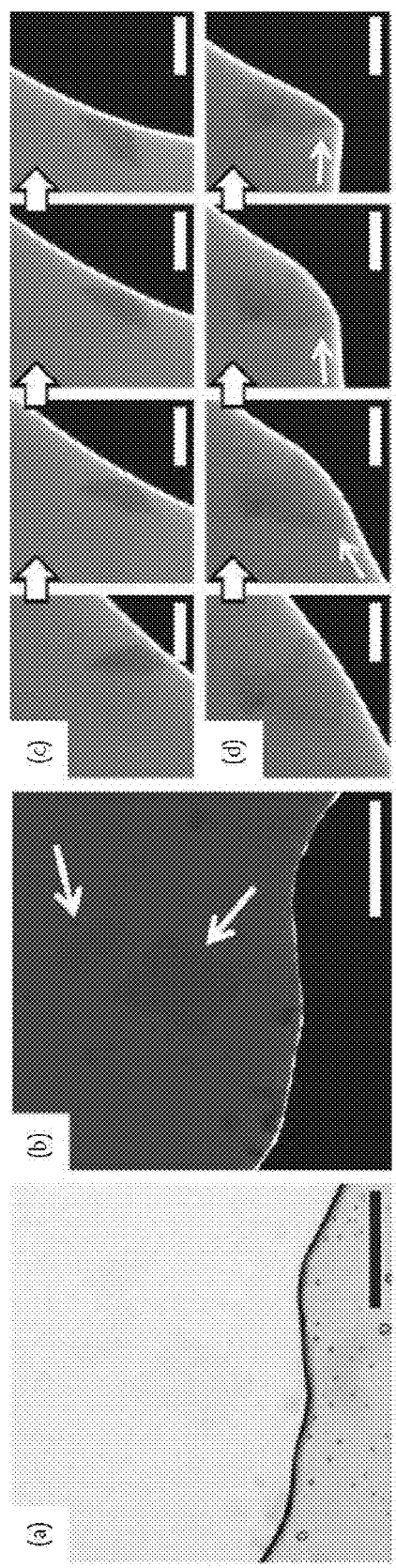
FIG. 9 shows an FQM allows direct, real-time, solution phase observation of GO sheets. (a) Under bright field, GO sheets suspended in an aqueous dilute fluorescein solution are barely visible. (b) When switched to FQM mode, GO appear as darker sheets. (c) and (d) are snapshots capturing the drifting and contact line pinning of GO sheets during dewetting process, respectively. Scale bars in (a-b)=50 μm, and (c-d)= 15 μm.

In one embodiment as shown in FIG. 9 and further described below, the liquid medium is water. The liquid medium can also be other solutions.

The visibility contrast, C, formed between the graphene-based film and the fluorescent coating satisfies the following relationship:

$$C=(I_B-I_G)/I_{B'}$$

wherein $I_B$ and $I_G$ are the optical intensities of the fluorescent coating and the graphene-based film in the imaging, and wherein $I_B > I_G$.

In one embodiment, the light 452 of a specific wavelength or wavelengths is delivered from a light source 402 of a fluorescence microscope 400. The light 452 of a specific wavelength or wavelengths is delivered onto the fluorescent coating of the sample 406 through an optical mirror 410 and then optical objective 404 during the illuminating step. The fluorescent coating has a thickness d<200 nm. The light 454 returned from the fluorescent coating of the sample 406 passes through optical objective 404 and may be other optical elements to reach detector 408 such as a camera with a viewer, which collects the returned light signals 454 and displays corresponding images accordingly.

Figure 6:
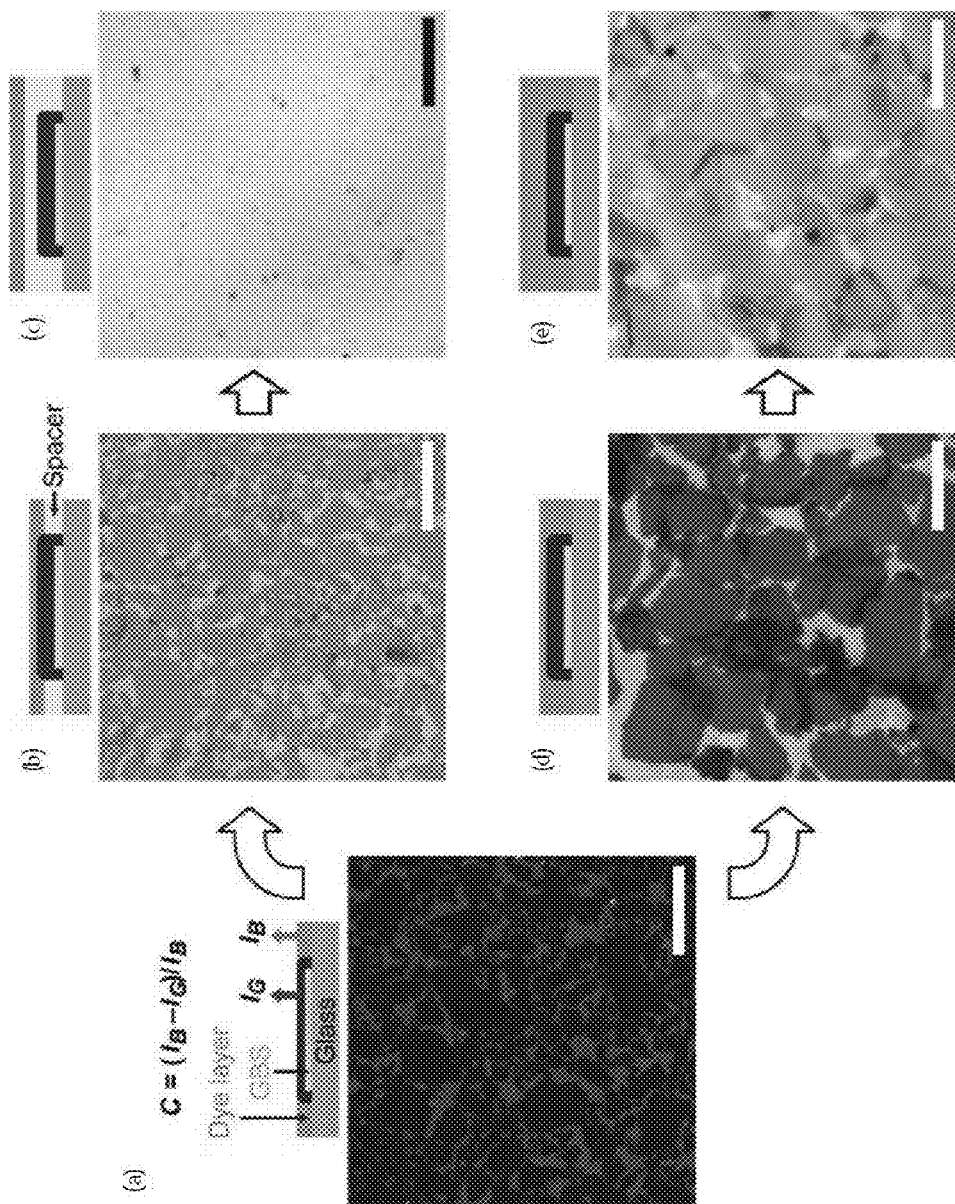
FIG. 6 show the effects of the thickness of a spacer layer (upper row) and the dye layer (bottom) on the FQM contrast. (a) When a thin dye layer (<5 nm) is applied, emission of all dye molecules above the sample can be quenched, resulting in maximal FQM contrast (C≈1). (b) With a 20 nm polystyrene spacer between the dye film and GO sheets, the contrast is decreased since there are excess dye molecules beyond GO's effective quenching distance. (c) With a 200 nm thick spacer, essentially no emission quenching is observed. (d) When a 30 nm thick dye layer is applied, the overall image contrast is decreased but the difference between single and multilayer becomes apparent due to incomplete emission quenching. (e) With a 200 nm coating, however, the overall contrast is much reduced, which hinders naked-eye observation. The optimal dye thickness was found to be in the range of 20 to 50 nm. All scale bars=50 μm. Adapted from[30], with permission, ACS Publication.

In one embodiment in FIG. 6 and further described in EXAMPLE 6, the method further includes the step of determining a thickness or a number of layers of the graphene-based film from the imaging of the graphene-based film.

In another aspect, the present invention provides a method for forming a pattern on a graphene-based film. In one embodiment as shown in FIG. 10 and further described in EXAMPLE 9, such a method 1000 includes the steps of (a) providing a graphene-based film 1002 supported by a substrate at step 1001, wherein the graphene-based film 1002 has one or more GO sheets or r-GO sheets or graphene sheets;

(b) forming a fluorescent photoresist coating 1004 over the graphene-based film 1002 to form a sample at step 1003;

(c) illuminating the sample with light of a first wavelength or wavelengths along an optical path such that a visibility contrast is formed between the graphene-based film and the fluorescent photoresist coating at step 1005*a*;

(d) imaging the graphene-based film from the visibility contrast to select a desired GO sheet or r-GO sheet or graphene sheet at step 1005*b*;

(e) inserting a photo mask 1006 in front of the selected GO sheet or r-GO sheet or graphene sheet along the light path, wherein the photo mask is formed with a plurality of windows that are transparent to optical energy, and wherein the plurality of windows is arranged according to a desired pattern at step 1007*a*; and (f) illuminating the photo mask with light of a second wavelength or wavelengths along the optical path to irradiate the sample by the optical energy passing through the plurality of windows of the photo mask to expose the fluorescent photoresist coating and form a pattern corresponding to the desired pattern on the selected GO sheet or r-GO sheet or graphene sheet at step 1007*b*.

Figures 10A, 10B:
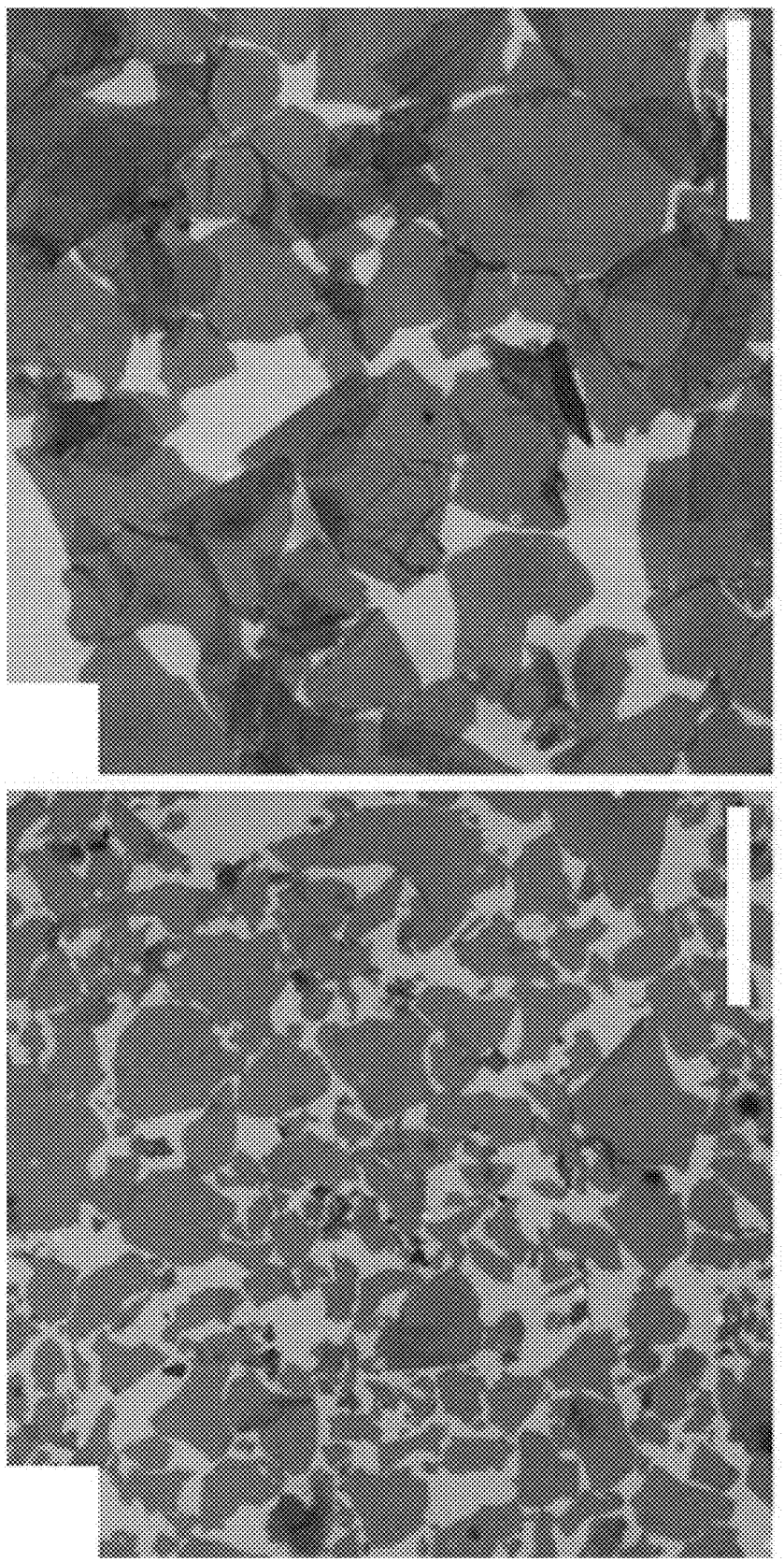
FIG. 10 is an Interfacing FQM imaging with photolithography. FQM images of GO sheets deposited on glass obtained with a 25 nm thick layer of DCM doped (A) photoresist SU-8 and (B) deep UV resist PMMA, respectively. Scale bars=50 μm. (C) Schematic illustration showing how FQM allows GBS to be seen through the resist layer during photolithography. First the GBS sample is visualized in a fluorescence microscope under an illuminating wavelength that is safe to the resist material. Then a photo mask can be inserted into the optical path to define exposed areas on a pre-selected sheet. Finally, the illuminating wavelength is switched to UV to expose the photoresist. As a proof of concept, the FQM images at the bottom show (left) a GO sheet deposited on glass and (right) a mask of 4 probe electrodes pattern superimposed onto the same sheet. Scale bars=20 μm.
Figure 10C:
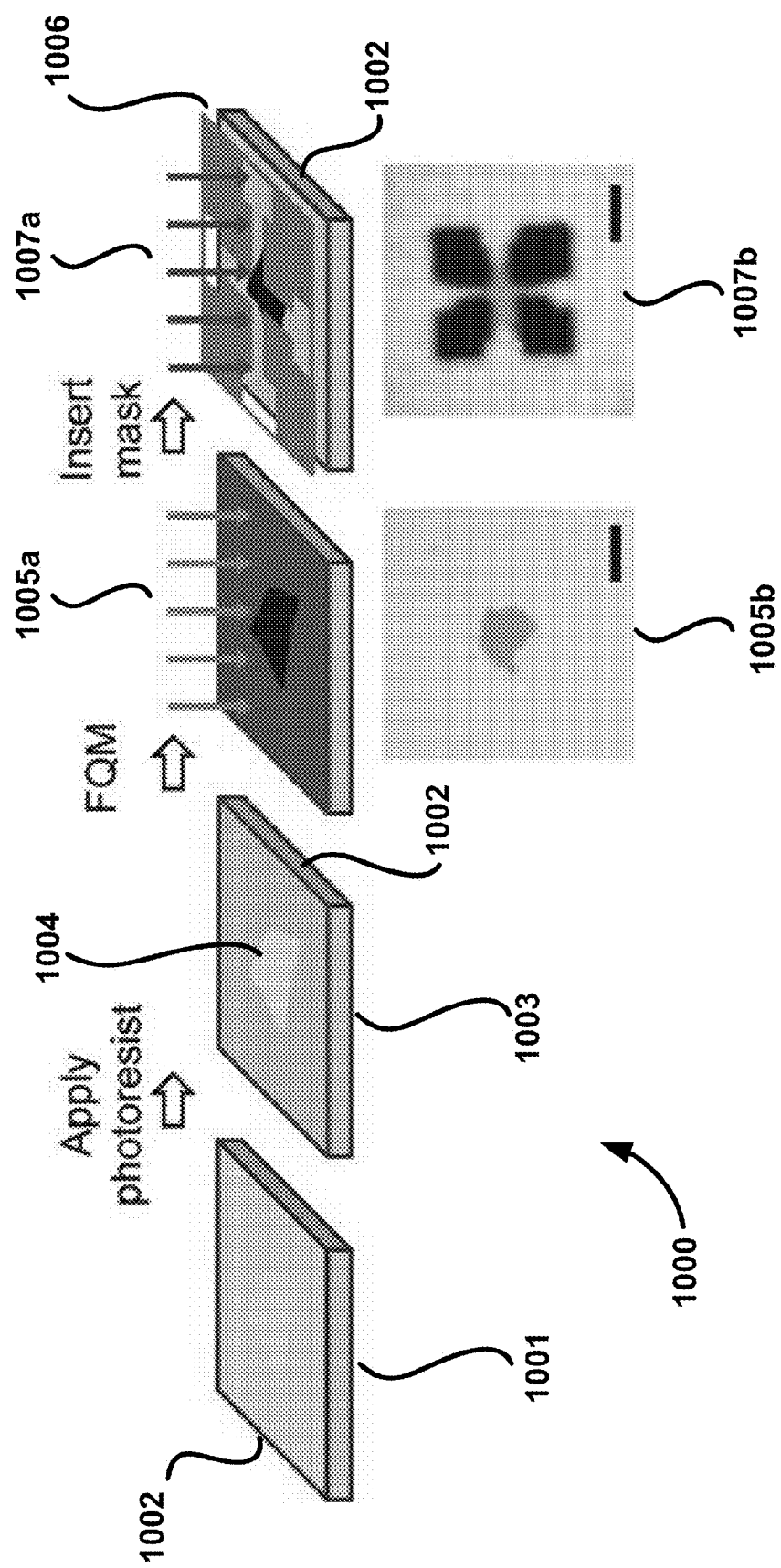

In one embodiment as shown in FIG. 10(C), the substrate is formed from glass.

In one embodiment, the fluorescent photoresist coating has a dye and polymer layer. The dye and polymer layer can be one of dye doped photoresist SU-8 layer and photoresist poly(methyl methacrylate) (PMMA) layer. As formed, the fluorescent photoresist coating layer contains a plurality of fluorescent dye molecules that a visibility contrast is formed between the graphene-based film and the fluorescent photoresist coating layer for determining the selected graphene based sheets.

The first specific wavelength is greater than 520 nm. In one embodiment as shown in FIG. 10(C), the light of the first specific wavelength is a green light with a frequency in a range of from about 520 nm to about 565 nm.

The second specific wavelength is smaller than the first specific wavelength. The second specific wavelength is smaller than 500 nm. In one embodiment as shown in FIG. 10(C), the light of the second specific wavelength is an ultraviolet light with a frequency in a range of from about 10 nm to about 400 nm.

In one embodiment, the light of the first specific wavelength is delivered from a light source such as light source 402 with a first filter cube, and the light of the second specific wavelength is delivered from the light source with a second filter cube.

The graphene-based film with a pattern as formed has a conducting area and an insulating area, and wherein the conducting area is formed with a pattern corresponding to the plurality of windows arranged according to a desired pattern by being exposed to the optical energy delivered through the plurality of windows of the mask, and the insulating area is formed corresponding to the areas of the mask where the plurality of windows are not located at, respectively. In one embodiment, the conducting area comprises an array of electrodes as shown in as shown in FIG. 10(C).

In another aspect, the present invention provides an article of manufacture made by the method as set forth immediately above.

EXAMPLES

Aspects of the present teachings may be further understood in light of the following examples, which should not be construed as limiting the scope of the present teachings in any way.

Example 1

Synthesis of graphene, graphene oxide (GO), and reduced graphene oxide (r-GO). Graphene was prepared by micromechanical cleavage of highly oriented pyrolytic graphite using the "Scotch Tape" method. GO was synthesized using a modified Hummers and Offeman's method from graphite powder (Bay carbon, SP-1). Chemically reduced graphene oxide (r-GO) was prepared by exposing GO-coated substrates to hot hydrazine vapor (Sigma Aldrich, anhydrous, 98%) in a sealed chamber maintained at 100° C. for overnight.

Example 2

Sample preparation. Glass microscope coverslips (VWR) and $SiO_2$/Si wafers were cleaned following standard RCA treatment method. Polyester substrates (Eppendorf) were cleaned with deionized water. GO film was deposited either by Langmuir-Blodgett technique[12] (Nima Technology, Medium size LB deposition trough) or by spin-coating (Laurell Technologies Corporation, WS-400, 1 min at 4000 rpm).

To prepare the dye/polymer coating, 1 mg of a green fluorescent dye-fluorescein sodium salt powder was added to 10 ml of polyvinylpyrrolidone (PVP, $M_W$=55,000)/ethanol solutions. Solutions with 0.1, 0.5, 1, and 5 wt % of PVP were prepared to vary the thickness of the coating. For the 5 wt % PVP solution, 2 mg of dye powder was added to compensate the fluorescence quenching by PVP. Next, 100 µl of coating solution was dispensed for each 0.5 $in^2$ of substrate area, and spun for 5 sec at 300 rpm and then 45 sec at 4000 rpm. The films produced from 0.5, 1, and 5 wt % of PVP solutions were measured to be approximately 10 nm, 30 nm, and 200 nm by profilometer, respectively. The thicknesses of films produced from 0.1 wt % PVP solution were found to be smaller than 5 nm, although the exact values were difficult to determine due to intrinsic surface roughness of the coverslips. The dye/polymer film was also prepared with a photoresist poly(methyl methacrylate) (PMMA, $M_W$=120,000) and a red florescent dye 4-(dicyanomethylene)-2-methyl-6-(4-dimethylaminostyryl)-4H-pyran (DCM, 98%). 0.5 mg of DCM was added to 10 ml of 0.5 wt % PMMA/chloroform solution. Then the solution was dispensed upon a substrate drop-wise (100 µl for each 0.5 $in^2$ substrate area) while spinning at 8000 rpm for 1 min, giving a thin dye film of approximately 25 nm thickness measured by profilometer. A blue fluorescent dye 2,5-Bis (5-tert-butyl-2-benzoxazolyl) thiophene (BBOT, >98%) was also tested. FQM imaging was achieved for all the three dyes. All chemicals, except for BBOT (TCI America), were purchased from Sigma-Aldrich, USA.

Example 3

Direct fluorescence microscopy imaging of GBS. Some GBS, such as GO has weak fluorescence in the visible and near-infrared region as shown in FIG. 3(a) (brown line), which in principle, can be utilized for visualization upon excitation. Fluorescence microscopy is a mature technique for identifying the positions of target objects in both solid and liquid forms, which has been especially useful for biological samples. Although GO nanosheets have been used as fluorescence label for cell imaging[46], unfortunately, it was found that the fluorescence of micron sized GO is too weak for real-time observation. FIG. 3(b) shows a dark field fluorescence image of GO sheets deposited on glass, in which the sheets can be clearly seen. However, it took about 10 seconds of signal integration time with the maximal excitation intensity to acquire this image by a cooled, high-sensitivity CCD camera (Photometrics CoolSNAP HQ2). r-GO is an even weaker emitter in the visible range as shown in FIG. 3(a) (black line), which makes it impractical to be visualized under the same imaging conditions. The inset in FIG. 3(c) shows an optical microscopy image of an r-GO film taken under bright field transmitted light. Some dark islands are visible, corresponding to the thick, multilayer aggregates. However, under the fluorescence mode, no feature is visible even over prolonged exposure time as shown in FIG. 3(c).

Example 4

Fluorescence quenching by GBS. To enhance or enable the visibility of objects of interest in fluorescence microscopy, a routine method is to brighten them up with fluorescent labels[47]. However, it has been well known that graphitic systems, such as carbon nanotubes[48,49] and graphite[50] itself are efficient fluorescence quenchers for dye molecules through both the short-range interactions such as electron or charge transfer, and long-range energy transfer. In fact, this effect has been utilized to reduce the fluorescence interference in Raman spectroscopy[50]. Recent theoretical[51,52] and experimental[53] studies indicate that GBS also strongly quenches the emission of nearby dye molecules. The inventors discovered that GO and r-GO are efficient fluorescence quenchers for dyes with very different molecular structures and absorbance/emission profiles. FIG. 4 shows the fluorescence spectra of three different dyes, namely fluorescein (green), 4-(dicyanomethylene)-2-methyl-6-(4-dimethylaminostyryl)-4H-pyran (DCM, red) and 2,5-bis(5-tert-butyl-2-benzoxazolyl)thiophene (BBOT, blue). The fluorescence intensities were significantly reduced upon the addition of small amount of r-GO, or even GO, regardless of the types of dyes, as shown in FIG. 4 (inset). The fluorescence quenching by GO is likely due to the residual graphitic domains that survived the severe oxidation process[25]. This result presents a great challenge for fluorescence imaging of graphitic materials by labeling, since the fluorescence from the attached molecules will likely be quenched. Although fluorescent labeling of carbon nanotubes has been reported, it relied on rather sophisticated chemical functionalization to insert a suitable nanospacer between the dye molecules and the carbon nanotubes to reduce emission quenching[54].

Example 5

Figure 4F:
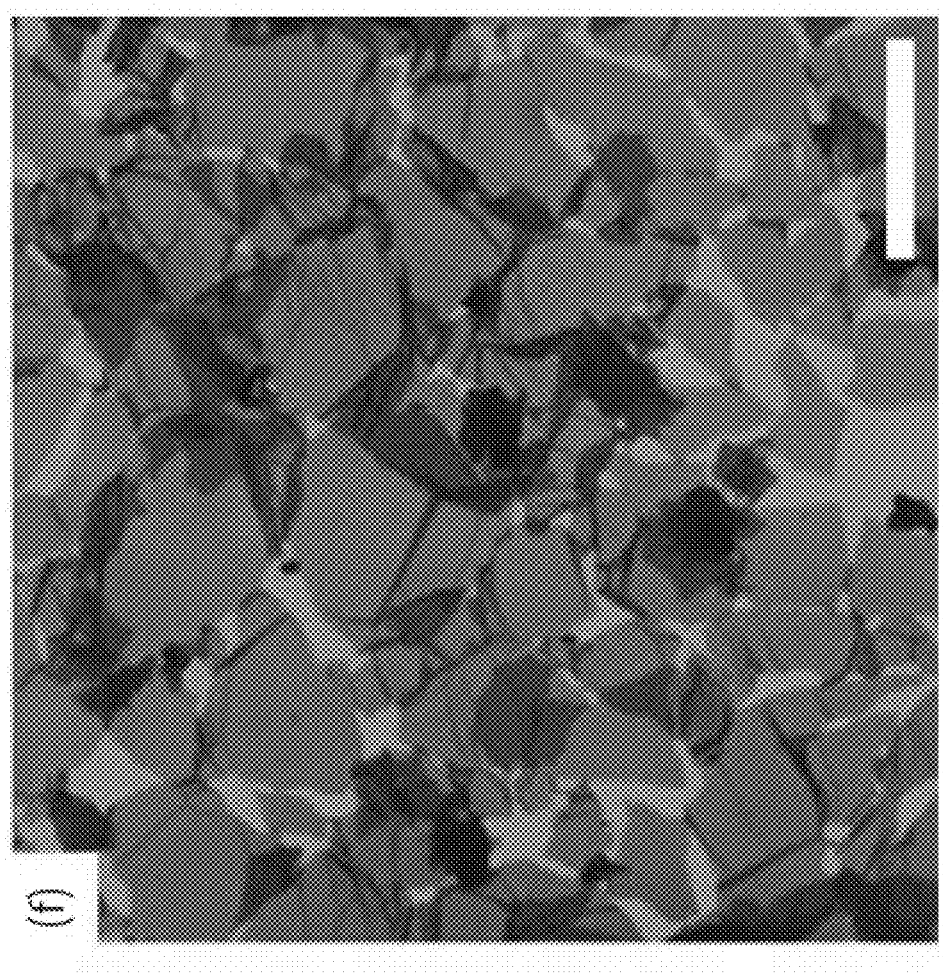

Fluorescence quenching microscopy of GBS. In a reverse strategy, a new imaging technique for GBS was invented and developed according to the present invention, namely fluorescence quenching microscopy (FQM). The underlying principle is essentially the opposite of the common fluorescence labeling method. Instead of being labeled to be bright, the GBS materials are made dark utilizing their strong quenching effect of fluorescent dyes. Typically this could be achieved by making a fluorescent coating on the GBS covered surface, which upon excitation could reveal the underlying GBS as dark sheets in a bright background as illustrated in FIGS. 4D and 4E, respectively. Ideal dye molecules should have high quantum yield and low cost. Fluorescein satisfies these criteria and thus is used as an exemplary, model material for most of the proof-of-concept experiments performed according to various embodiments of the present invention. A small amount of polymer such as polyvinylpyrrolidone (PVP) is co-dissolved in dye solution to improve the uniformity of the dye coating. FIG. 4F shows an FQM image of GO sheets deposited on a $SiO_2$/Si substrate with fluorescein/PVP coating. It reveals vivid details of underlying GO film, including wrinkles, folds and overlaps that can also be seen directly by naked-eye observation through the eye pieces. Since the fluorescence quenching effect by GBS is strong enough to generate stark contrast against the bright background, FQM can produce high-contrast images comparable to those taken by SEM or AFM, with much simpler and cheaper instrument set up as shown in FIG. 4E. Mechanically exfoliated graphene and r-GO have higher quenching efficiency, and thus can be easily observed by FQM, too[30].

Figure 5:
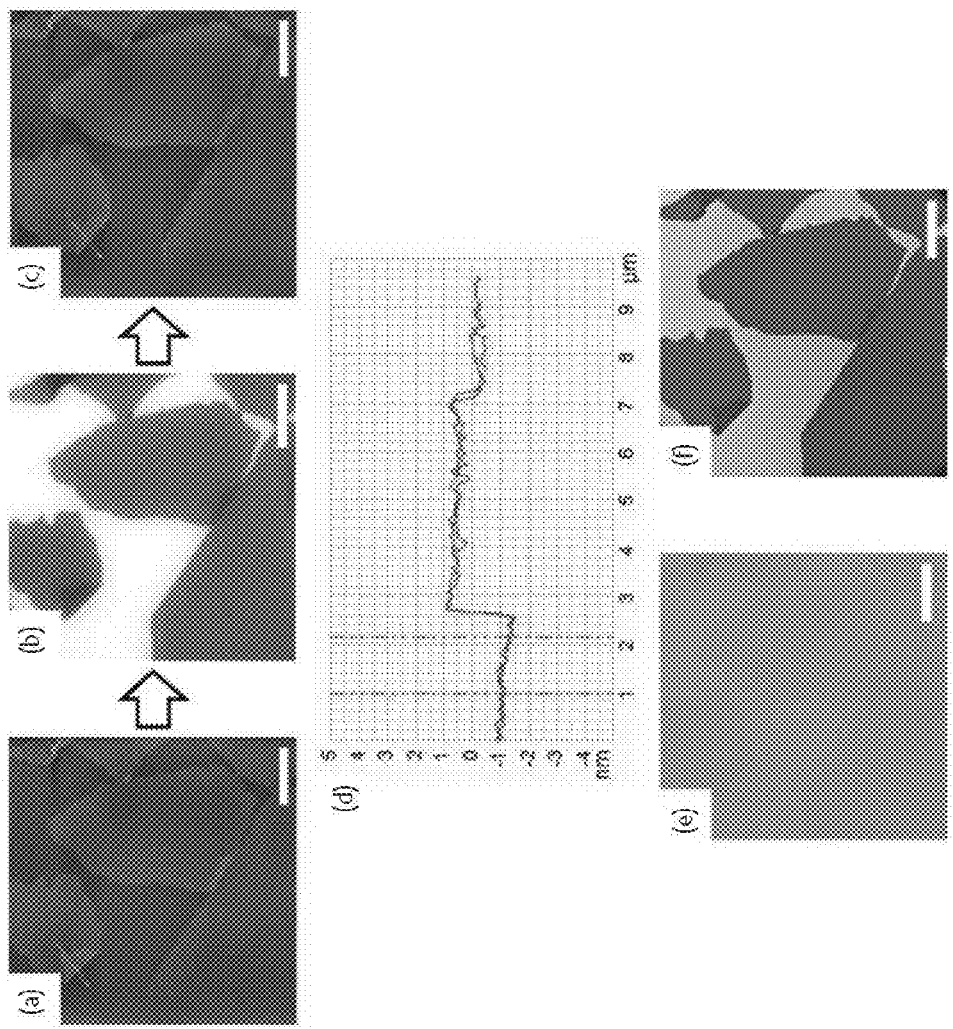
FIG. 5 shows an AFM image of GO sheets deposited on $SiO_2$/Si substrate showing single layers and folded double layers. (b) FQM image of the same area after spin-coating a fluorescein/PVP thin film, which perfectly match the AFM view in (a). The dye layer can be easily removed by brief washing with water or ethanol. (c) AFM image of the same area after dye removal shows that the underlying GO sheets were not disrupted or contaminated by the FQM process. (d) Line scans of a GO double layer before and after dye coating show no significant deviation in thickness, suggesting that FQM can be non-destructive. Compared to (e) the reflectance optical microscopy image, (b) FQM image can offer much improved contrast and layer resolution comparable to (a) AFM and (f) SEM images. All scale bars=10 μm.

Comparison of AFM, as shown in FIG. 5(a), and FQM, as shown in FIG. 5(b), images taken at the same sample area confirms that the image generated by fluorescence quenching truly represents the morphology of GBS. Height profile of AFM measurement shows that the GO sheet shown in upper left corner of the area is a single layer with a folded edge as shown in FIG. 5(d). In the FQM image, the folded area appears darker than the single layer domains. Since the apparent thickness of GO was measured to be around 1 $nm^{24}$, the higher degree of quenching by double layers suggests that the underlying quenching mechanism is likely based on a long range effect such as resonance energy transfer through dipole-dipole interactions[51,52,55]. In contrast, the short-range mechanisms are less useful for imaging as they are unlikely to resolve the difference between single and multilayers, which would not be capable to reveal the important morphological factors such as wrinkles, folds, overlaps or number of layers[56]. FIG. 5 thus demonstrates the layer counting capability of FQM. After FQM imaging, the dye layer can be easily removed by brief washing with solvents. For example, the AFM image of the same GO sheets after rinsing off the fluorescein/PVP layer as shown in FIG. 5(c) appears identical to the one before applying the dye layer as shown in FIG. 5(a), so does the height profile of the folded area as shown in FIG. 5(d). No contamination or change in sheet morphology can be detected in both FIGS. 5(c) and 5(d), respectively. Due to the large surface area of GBS, their van der Waals adhesion[57] to the substrates is strong enough to protect them from multiple spin-coating and washing steps, thus making FQM non-destructive. The images of the same sample areas as shown in FIG. 5 were obtained by various means, more specifically, FIGS. 5(a) and (c) by AFM imaging, FIG. 5(b) by FQM imaging, FIG. 5 (e) by reflectance optical microscopy, and FIG. 5(f) by SEM imaging, respectively. It can be clearly seen that FQM imaging according to one embodiment of the present invention offers drastic improvement over reflectance optical microscopy. Its resolution and layer contrast are comparable to AFM imaging and SEM imaging, respectively.

Example 6

Resolution and contrast of FQM. Being a light based technique, the lateral resolution of FQM is diffraction limited. However, it is well suited for observing micron-sized sheets, which happens to align well with the increasing demand for synthesizing larger GBS materials[58]. The contrast of FQM originates from emission quenching by GBS, which creates dark regions in the bright fluorescent layer upon excitation. The visibility contrast can be described as $$C=(I_B-I_G)/I_B,$$

where $I_B$ and $I_G$ are the optical intensities of the background and the GBS domains in a FQM image, respectively, as shown in FIG. 6(a). C represents a measure of percentage quenching. $I_B$-$I_G$ is related to the depth of quenching extended into the dye layer, or the effective quenching distance. It can be defined as the maximal separation between GBS surface and the dye molecules, at which the rate of energy transfer becomes comparable to the natural fluorescence decay rate of the dye molecule (i.e., when the presence of GBS no longer quenches the dye emission)[55]. If the dye layer thickness is thinner than the quenching distance, the emission from the entire dye layer above the GBS could be quenched, in which case pne has $I_G \approx 0$ and $C \approx 1$. Indeed, with a fluorescein/PVP layers thinner than 5 nm, nearly full contrast (C=0.98) was observed in the FQM image of GO sheets as shown in FIG. 6(a). When a 20 nm thick, non-fluorescent polystyrene (PS) layer is inserted between GO sheets and the dye coating as a nano-spacer, the contrast of GO decreases, as shown in FIG. 6(b). No fluorescence quenching can be observed with a 200 nm thick spacer as shown in FIG. 6(c). Recent theoretical studies show that graphene is an excellent long-range fluorescence quencher with an effective quenching distance extends up to 30 nm. These examples performed according to various embodiment of the present invention clearly demonstrate that even GO has the long-range quenching capability. FIGS. 6(b) and 6(c) suggest that the effective quenching distance for GO, which is a weaker quencher, should also be on the order of tens of nanometers. The long-range quenching effect will make the GBS appear slightly larger by tens of nanometers in FQM images, but this is negligible compare to the intrinsic resolution limit of optical microscopy—the wavelength of visible light. Therefore, the lateral resolution of FQM will not be compromised.

Although thinner dye layer produces higher FQM contrast, which can facilitate the detection of GBS materials, it also results in an "over-saturated" condition where C≈1 for all the sheets, regardless of their thickness (number of layers). This is not suitable for resolving the number of layers, or the degree of overlapping between neighboring sheets. When the dye coating is thicker than the effective quenching distance, there is a layer of dye materials beyond the "reach" of the GBS as shown in FIG. 6(d), therefore they remain bright upon excitation. This decreases the overall contrast, but turns out to be beneficial for imaging since it helps to reveal more details in the image. Multilayers of GBS pieces can quench the emission of more dye molecules above them, thus appearing darker than monolayers as shown in FIGS. 6(d) and 6(e), respectively. The optimal thickness of the fluorescein/PVP coating to ensure layer counting capability, while maintaining high overall contrast, was measured to be in the range of 20 to 50 nm. Within this range, vivid details, such as overlaps, wrinkles and folds, of underlying GBS materials can be readily observed by naked eye.

Example 7

Figure 7:
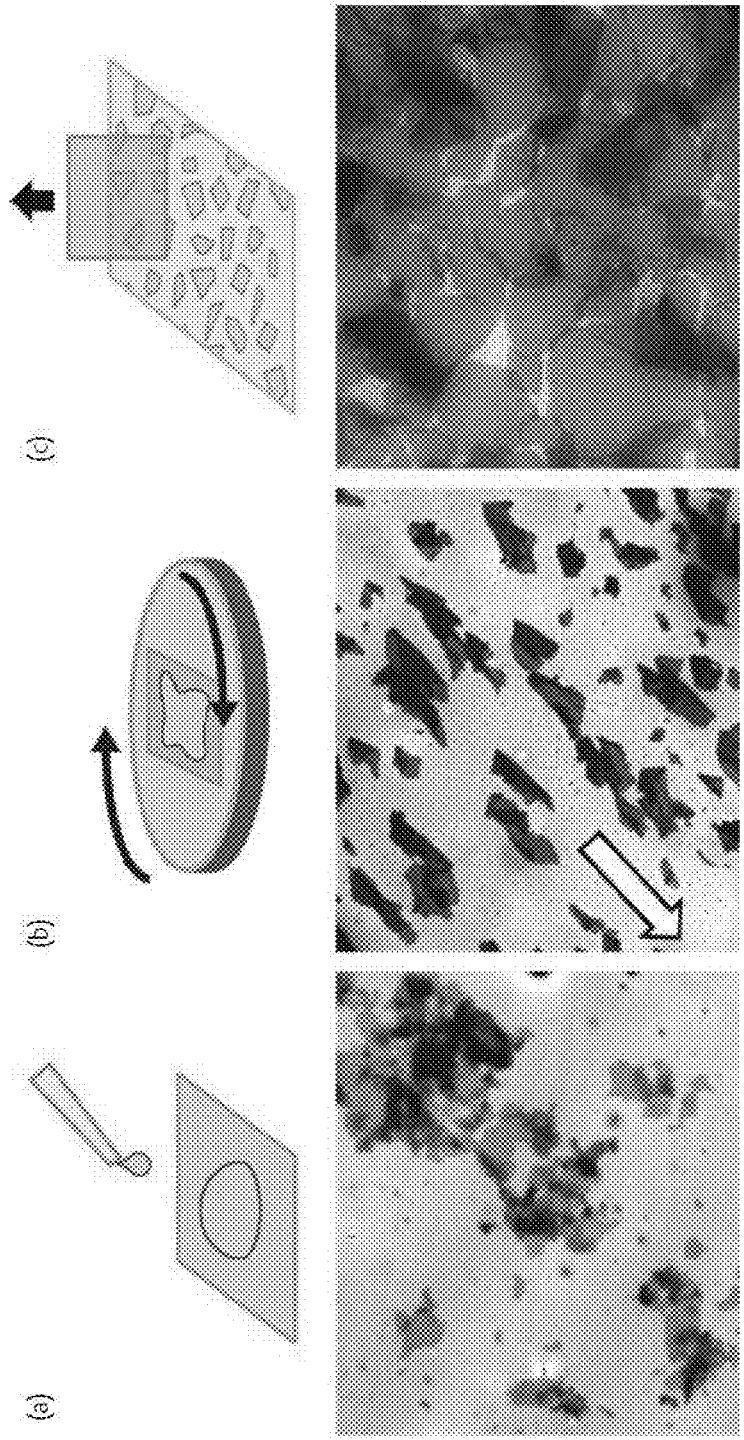
FIG. 7 is an FQM imaging of GO sheets deposited on polyester slides by (a) drop casting, (b) spin coating and (c) LB assembly. (a) Drop casting and (b) spin coating make GO sheets heavily wrinkled and folded during the process, which reduces the surface coverage of resulting films. (c) In contrast, LB can produce a large-area monolayer of GO sheets with much higher surface coverage. All scale bars=50 μm.
Figure 8:
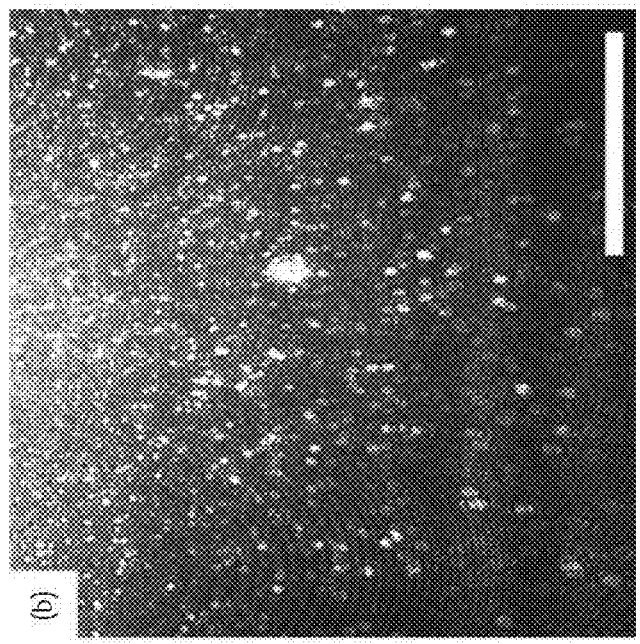
FIG. 8 is a Brewster angle microscopy (NIMA MicroBAM) image of GO sheets floating on air-water interface. (a) The change of the Brewster condition (53° for water surface) induced by GO monolayer on aqueous surface enables the p-polarized light to reflect, resulting in bright spots against dark background in the BAM image shown in (b). Scale bar=1 mm.
Figure 8:
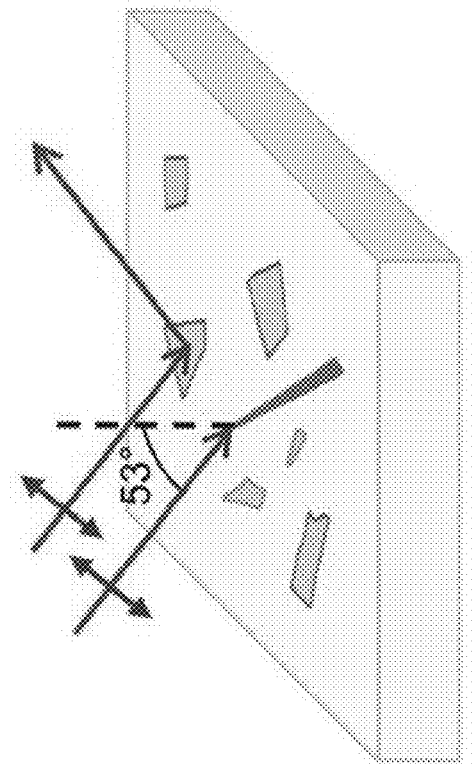

Evaluating GBS films deposited on plastic substrates. Plastic supported GBS films have great promise as a component in cheap, flexible electronic devices and surface protective coatings. Typically, such films are created by solution processing[7,9,12,59,60] such as dip-coating, drop-casting, spraying or spin-coating using GBS dispersion. The properties of the final thin films are determined largely by surface coverage and morphology of the individual sheets, which are heavily dependent on the synthetic and processing techniques. For example, excessive degree of wrinkles and folds will reduce the surface coverage and increase the roughness, which will deteriorate their performance as electrodes. However, it has been a great challenge to image such thin films using current imaging techniques since common plastic substrates are insulating, amorphous and may not be smooth enough for AFM imaging. FQM practiced according to various embodiment of the present invention is particularly suitable for this task, since it lifts the need for special substrates. FIG. 7 shows FQM images of GO sheets deposited on polyester substrates, processed by three different techniques, namely drop casting as shown in FIG. 7(a), spin coating as shown in FIG. 7(b) and Langmuir-Blodgett (LB) assembly as shown in FIG. 7(c)[36]. It can be clearly seen that uncontrolled dewetting process, as occurred in drop-casting and spin-coating, tends to produce heavily wrinkled and folded GO sheets. Furthermore, GO sheets were found to be stretched along the solvent spreading direction during spin-coating. The high degree of wrinkles and folds reduces the surface coverage of GO sheets on plastic substrate, which is not desirable for the application as transparent electrode. In contrast, LB assembly produces nearly fully covered GO thin film, as shown in FIG. 7(c). Therefore, FQM can be used as a high-contrast, quality control tool to evaluate GBS thin films, thus helping one to design the best processing conditions and the proper surface treatment of plastic substrates.

Example 8

Direct observation of "wet" GBS. Direct observation of "wet" GBS materials can help to reveal their conformations or dynamic assembly behaviors without the interference of dewetting force or substrate interactions. However, the need for special substrates in current imaging techniques prohibits direct observation of GBS in solution. Brewster angle microscopy (BAM)[61,62] can visualize molecular monolayer films at the air-water interface, including GO sheets[36,63]. The reflectivity of plane-polarized (p-polarized) light becomes zero at the Brewster angle (53° for air-water interface) on bare water surface. If there is a molecular monolayer on water surface, however, it changes the Brewster condition, resulting in the reflection of p-polarized light in that area as shown in FIG. 8(a). Therefore, molecular monolayer appears brighter than background in a BAM image. BAM can be a useful tool to observe the dynamic assembly behaviors of GBS on water surface as shown in FIG. 8(b). However, BAM with resolution sufficient for revealing the single layer details has not been made widely available yet. Many interesting phenomena of GBS materials could occur "inside" the liquid, especially for those synthesized and processed in a form of dispersion. For instance, the dynamic solution behavior of GO sheets during solvent evaporation is critical to determine the final film morphology. Understanding such behaviors is important towards establishing a structure-properties relationship for solution-processed GO thin films. However, direct observation of GBS in solution has not been demonstrated yet. By practicing FQM according to various embodiments of the present invention, it is now possible to visualize them in solution. FIG. 9(a) is a bright field image of an evaporating GO/fluorescein aqueous droplet. Although the air-water contact line can be clearly seen, GO sheets are barely visible. When switched to FQM mode, however, GO becomes readily visible as dark sheets as shown in FIG. 9(b). Real-time observation of the dynamic solution behaviors of individual GBS piece is now possible with FQM. Two general dewetting behaviors of GO sheets were observed by practicing the present invention in one embodiment, namely, drifting as shown in FIG. 9(c) and crumpling as shown in FIG. 9(d), respectively. Small GO sheets tend to drift along with the receding contact line, during which they rotate until one of its longer edges is aligned with the contact line. Larger, more flexible GO sheets often become pinning sites for the receding contact line. Then the capillary force imposed by dewetting can often fold them up into a heavily crumpled geometry. Thus, real-time FQM observation explains the presence of large amount of wrinkled, folded and overlapped sheets in drop-casted GO films.

Example 9

FQM based microfabrication. The dye/polymer coating for FQM can be easily washed away if necessary. However, it can also be "utilized" for further processing according to various embodiments of the present invention. FQM is independent of the types of dyes and polymers used to form the fluorescent dye layer. High quality FQM images of GO sheets have been obtained using dye doped photoresist SU-8 and deep UV resist poly(methyl methacrylate) (PMMA) as shown in FIGS. 10A and 10B, respectively. Since the photoresist coating is required during microfabrication of devices, SU-8 or PMMA based FQM according to various embodiments of the present invention is fully compatible with photolithography processes. In one embodiment, lithography is practiced without the need for alignment marks since GBS, regardless of the substrate, can now be seen through the photoresist layer by the FQM. As illustrated in FIG. 10C, one can first illuminate the sample with lower energy photons (e.g., green) that are safe for the resist materials, find the suitable sheets, and then insert a photo mask in the optical path of the microscope to define the exposed areas. Note that with a fluorescence microscope, this can be conveniently done by switching filter cubes of different exciting wavelengths. Therefore, FQM should be able to extend the "on-sheet" GBS device fabrication capability to flexible, plastic substrates. For example, FQM can be coupled with the microscope projection photolithography technique[64] to make devices. As a proof of concept, a GO sheet deposited on glass slide was first selected using FQM, and then a photo mask was inserted in the field diaphragm of a fluorescence microscope to project the electrodes pattern onto the same identified GO sheet as shown in FIG. 10C (bottom).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

References

1. Novoselov, K. S., et al., *Science* (2004) 306, 666. 34. Jung, I., et al., *J. Phys. Chem. C* (2008) 112, 8499.
2. Allen, M. J., et al., *Chem. Rev.* (2010) 110 (1), 132. 35. Stolyarova, E., et al., *Proc. Natl. Acad. Sci.* (2007) 104, 9209.
3. Park, S., and Ruoff, R. S., *Nature Nanotech.* (2009) 4, 217. 36. Cote, L. J., et al., *J. Am. Chem. Soc.* (2009) 131, 1043
4. Geim, A. K., *Science* (2009) 324, 1530. 37. Ferrari, A. C., et al., *Phys. Rev. Lett.* (2006) 97, 187401.
5. Kim, K. S., et al., *Nature* (2009) 457, 706. 38. Graf, D., et al., *Solid State Commun.* (2007) 143, 44.
6. Li, X. L., et al., *Science* (2008) 319, 1229. 39. Calizo, I., et al., *Solid State Commun.* (2009) 149, 1132.
7. Gilje, S., et al., *Nano Lett.* (2007) 7, 3394. 40. Krauss, B., et al., *Phys. Rev. B* (2009) 79, 165428.
8. Li, X. L., et al., *Nature Nanotech.* (2008) 3, 538. 41. Cote, L. J., et al., *J. Am. Chem. Soc.* (2009) 131, 11027.
9. Wang, X., et al., *Nano Lett.* (2008) 8, 323. 42. Jung, I., et al., *Nano Lett.* (2008) 8, 4283.
10. Watcharotone, S., et al., *Nano Lett.* (2007) 7, 1888. 43. Hwa, T., et al., *Phys. Rev. A* (1991) 44, 82235.
11. Eda, G., et al., *Nature Nanotech.* (2008) 3, 270. 44. Wen, X., et al., *Nature* (1992) 355, 426.
12. Tung, V. C., et al., *Nature Nanotech.* (2009) 4, 25. 45. Spector, M. S., et al., *Phys. Rev. Lett.* (1994) 73, 2867.
13. Stankovich, S., et al., *Nature* (2006) 442, 282. 46. Sun, X., et al., *Nano Res.* (2008) 1, 203.
14. Ramanathan, T., et al., *Nature Nanotech.* (2008) 3, 327. 47. Llopis, J., et al., *Proc. Natl. Acad. Sci.* (1998) 95, 6803.
15. Dobelle, W. H., and Beer, M., *J. Cell Biol.* (1968) 39, 733. 48. Liangwei, Q., et al., *J. Chem. Phys.* (2002) 117, 8089.
16. Meyer, J. C., et al., *Nature* (2008) 454, 319. 49. Nakayama-Ratchford, N., et al., *J. Am. Chem. Soc.* (2007) 129, 2448.
17. Lee, Z., et al., *Nano Lett.* (2009) 9 (9), 3365. 50. Kagan, M. R., and McCreery, R. L., *Anal. Chem.* (1994) 66, 4159.
18. Emtsev, K. V., et al., *Nature Mater.* (2009) 8, 203. 51. Swathi, R. S., and Sebastian, K. L., *J. Chem. Phys.* (2008) 129, 054703.
19. Yu, Q. K., et al., *Appl. Phys. Lett.* (2008) 93, 113103. 52. Swathi, R. S., and Sebastian, K. L., *J. Chem. Phys.* (2009) 130, 086101.
20. Li, X. S., et al., *Science* (2009) 324, 1312. 53. Xu, Y. F., et al., *Adv. Mater.* (2009) 21, 1275.
21. REINA, A., ET AL., *NANO LETT.* (2009) 9, 30. 54. DIDENKO, V. V., ET AL., *NANO LETT.* (2005) 5, 1563.
22. Hirata, M., et al., *Carbon* (2004) 42, 2929. 55. Turro, N. J., et al., *Principles of molecular photochemistry: An introduction*. University Science Books: Sausalito, Calif., 2009, pp. 495.
23. Dikin, D. A., et al., *Nature* (2007) 448, 457.
24. Stankovich, S., et al., *Carbon* (2007) 45, 1558.
25. Hummers, W. S., and Offeman, R. E., *J. Am. Chem. Soc.* (1958) 80, 1339.
26. Gao, W., et al., *Nature Chem.* (2009) 1, 403.
27. Widenkvist, E., et al., *J. Phys. D: Appl. Phys.* (2009) 42, 5.
28. Hernandez, Y., et al., *Nature Nanotech.* (2008) 3, 563.
29. Choucair, M., et al., *Nature Nanotech.* (2009) 4, 30.

30. Kim, J., et al., *J. Am. Chem. Soc.* (2010), 132 (1), 260.
31. Nair, R. R., et al., *Science* (2008) 320, 1308.
32. Jung, I., et al., *Nano Lett.* (2007) 7, 3569.
33. Roddaro, S., et al., *Nano Lett.* (2007) 7, 2707.
34. Jung, I., et al., J. Phys. Chem. C (2008) 112, 8499.
35. Stolyarova, E., et al., Proc. Natl. Acad. Sci. (2007) 104, 9209.
36. Cote, L. J., et al., J. Am. Chem. Soc. (2009) 131, 1043.
37. Ferrari, A. C., et al., Phys. Rev. Lett. (2006) 97, 187401.
38. Graf, D., et al., Solid State Commun. (2007) 143, 44.
39. Calizo, I., et al., Solid State Commun. (2009) 149, 1132.
40. Krauss, B., et al., Phys. Rev. B (2009) 79, 165428.
41. Cote, L. J., et al., J. Am. Chem. Soc. (2009) 131, 11027.
42. Jung, I., et al., Nano Lett. (2008) 8, 4283.
43. Hwa, T., et al., Phys. Rev. A (1991)
44. 82235.44. Wen, X., et al., Nature (1992) 355, 426.
45. Spector, M. S., et al., Phys. Rev. Lett. (1994) 73, 2867.
46. Sun, X., et al., Nano Res. (2008) 1, 203.
47. Llopis, J., et al., Proc. Natl. Acad. Sci. (1998) 95, 6803.
48. Liangwei, Q., et al., J. Chem. Phys. (2002) 117, 8089.
49. Nakayama-Ratchford, N., et al., J. Am. Chem. Soc. (2007) 129, 2448.
50. Kagan, M. R., and McCreery, R. L., Anal. Chem. (1994) 66, 4159.
51. Swathi, R. S., and Sebastian, K. L., J. Chem. Phys. (2008) 129, 054703.
52. Swathi, R. S., and Sebastian, K. L., J. Chem. Phys. (2009) 130, 086101.
53. Xu, Y. F., et al., Adv. Mater. (2009) 21, 1275.
54. Didenko, V. V., et al., Nano Lett. (2005) 5, 1563.
55. Turro, N. J., et al., Principles of molecular photochemistry: An introduction. University Science Books: Sausalito, Calif., 2009, pp. 495.
56. Treossi, E., et al., J. Am. Chem. Soc. (2009) 131, 15576.
57. Israelachvili, J. N., Intermolecular and Surface Forces. 2nd ed.; Academic Press: 1992, pp. 450.
58. Luo, Z. T., et al., J. Am. Chem. Soc. (2009) 131, 898.
59. Li, D., et al., Nature Nanotech. (2008) 3, 101.
60. Becerril, H. A., et al., ACS Nano (2008) 2, 463.
61. Danauskas, S. M, et al., Rev. Sci. Instrum. (2007) 78, 103705.
62. Marshall, G., et al., Rev. Sci. Instrum. (1998) 69, 3699.
63. Kim, F., et al., Adv. Mater. (2010), in press.
64. Love, J. C., et al., Langmuir (2001) 17, 6005.

What is claimed is:

1. A method for imaging a graphene-based film, comprising:
   (a) providing a graphene-based film on a surface of a medium;
   (b) forming a fluorescent coating over the graphene-based film to form a sample;
   (c) illuminating the sample with light of a specific wavelength or wavelengths, which is absorbed by the fluorescent coating to cause the fluorescent coating to emit light of wavelengths longer than that of the absorbed light, which is quenched by the graphene-based film such that a visibility contrast is formed between the graphene-based film and the fluorescent coating; and
   (d) imaging the graphene-based film from the visibility contrast.

2. The method of claim 1, wherein the graphene-based film comprises at least one of a GO sheet, a r-GO sheet, and a graphene sheet.

3. The method of claim 1, wherein the fluorescent coating comprises one of a dye layer and a dye and polymer layer.

4. The method of claim 3, wherein the dye comprises fluorescein, 4-(dicyanomethylene)-2-methyl-6-(4-dimethylaminostyryl)-4H-pyran, and 2,5bis(5-tert-butyl-2-benzoxazolyl)thiophene.

5. The method of claim 4, wherein the polymer comprises one of polyvinylpyrrolidone (PPV), poly(methyl methacrylate) (PMMA), and SU-8.

6. The method of claim 1, wherein the medium is solid or liquid.

7. The method of claim 6, wherein the solid medium comprises a substrate.

8. The method of claim 6, wherein the liquid medium comprises a solution.

9. The method of claim 1, wherein the visibility contrast, C, formed between the graphene-based film and the fluorescent coating satisfies the following relationship:

$$C=(I_B-I_G)/I_B,$$

where $I_B$ and $I_G$ are the optical intensities of the fluorescent coating and the graphene-based film in the imaging, and wherein $I_B > I_G$.

10. The method of claim 1, wherein the light of a specific wavelength or wavelengths is delivered from a light source of a fluorescence microscope.

11. The method of claim 1, wherein the light of a specific wavelength or wavelengths is delivered onto the fluorescent coating during the illuminating step.

12. The method of claim 1, wherein the fluorescent coating has a thickness d<200 nm.

13. The method of claim 1, further comprising the step of determining a thickness or a number of layers of the graphene-based film from the imaging of the graphene-based film.

14. A method for forming a pattern on a graphene-based film, comprising:
   (a) providing a graphene-based film supported by a substrate, wherein the graphene-based film has one or more GO sheets or r-GO sheets or graphene sheets;
   (b) forming a fluorescent photoresist coating over the graphene-based film to form a sample;
   (c) illuminating the sample with light of a first wavelength or wavelengths along an optical path such that a visibility contrast is formed between the graphene-based film and the fluorescent photoresist coating;
   (d) imaging the graphene-based film from the visibility contrast to select a desired GO sheet or r-GO sheet or graphene sheet;
   (e) inserting a photo mask in front of the selected GO sheet or r-GO sheet or graphene sheet along the light path, wherein the photo mask is formed with a plurality of windows that are transparent to optical energy, and wherein the plurality of windows is arranged according to a desired pattern; and
   (f) illuminating the photo mask with light of a second wavelength or wavelengths along the optical path to irradiate the sample by the optical energy passing through the plurality of windows of the photo mask to expose the fluorescent photoresist coating and form a pattern corresponding to the desired pattern on the selected GO sheet or r-GO sheet or graphene sheet.

15. The method of claim 14, wherein the substrate is formed from glass.

16. The method of claim 14, wherein the fluorescent photoresist coating comprises a dye and polymer layer.

17. The method of claim 16, wherein dye and polymer layer comprises one of dye doped photoresist SU-8 layer and photoresist poly(methyl methacrylate) (PMMA) layer.

18. The method of claim 14, wherein the visibility contrast, C, formed between the graphene-based film and the fluorescent photoresist coating satisfies the following relationship:

$$C=(I_B-I_G)/I_B,$$

where $I_B$ and $I_G$ are the optical intensities of the fluorescent photoresist coating and the graphene-based film in the imaging, and wherein $I_B > I_G$.

19. The method of claim 14, wherein the first specific wavelength is greater than 520 nm.

20. The method of claim 19, wherein the light of the first specific wavelength is a green light with a frequency in a range of from about 520 nm to about 565 nm.

21. The method of claim 19, wherein the second specific wavelength is smaller than the first specific wavelength.

22. The method of claim 21, wherein the second specific wavelength is smaller than 500 nm.

23. The method of claim 22, wherein the light of the second specific wavelength is an ultraviolet light with a frequency in a range of from about 10 nm to about 400 nm.

24. The method of claim 14, wherein the light of the first specific wavelength is delivered from a light source with a first filter cube, and the light of the second specific wavelength is delivered from the light source with a second filter cube.

25. The method of claim 14, wherein the graphene-based film with a pattern as formed has a conducting area and an insulating area, and wherein the conducting area is formed with a pattern corresponding to the plurality of windows arranged according to a desired pattern by being exposed to the optical energy delivered through the plurality of windows of the mask, and the insulating area is formed corresponding to the areas of the mask where the plurality of windows are not located at, respectively.

26. The method of claim 25, wherein the conducting area comprises an array of electrodes.

* * * * *